United States Patent
Tanaka et al.

(10) Patent No.: US 9,803,024 B2
(45) Date of Patent: Oct. 31, 2017

(54) ANTI-HUMAN PAI-1 ANTIBODY

(71) Applicant: Astellas Pharma Inc., Chuo-ku, Tokyo (JP)

(72) Inventors: Hirotsugu Tanaka, Tokyo (JP); Masayasu Yoshino, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 15/120,257

(22) PCT Filed: Feb. 20, 2015

(86) PCT No.: PCT/JP2015/054704
§ 371 (c)(1),
(2) Date: Aug. 19, 2016

(87) PCT Pub. No.: WO2015/125904
PCT Pub. Date: Aug. 27, 2015

(65) Prior Publication Data
US 2016/0369008 A1   Dec. 22, 2016

(51) Int. Cl.
*C07K 16/38* (2006.01)
*A61K 39/395* (2006.01)
*A61K 39/00* (2006.01)

(52) U.S. Cl.
CPC ........ *C07K 16/38* (2013.01); *A61K 39/39533* (2013.01); *A61K 2039/505* (2013.01); *A61K 2039/507* (2013.01); *C07K 2317/21* (2013.01); *C07K 2317/24* (2013.01); *C07K 2317/33* (2013.01); *C07K 2317/565* (2013.01); *C07K 2317/76* (2013.01); *C07K 2317/94* (2013.01); *C12N 2510/02* (2013.01)

(58) Field of Classification Search
None
See application file for complete search history.

(56) References Cited

U.S. PATENT DOCUMENTS 7,771,720 B2 * 8/2010 Staunton ................ C07K 16/36
424/133.1
2010/0254979 A1   10/2010 Staunton et al.

FOREIGN PATENT DOCUMENTS

| EP | 0320840 A2 * | 12/1988 | |
| WO | WO 02/34776 A2 | 5/2002 | |
| WO | WO 2004041155 A2 * | 5/2004 | ........... A61K 31/355 |
| WO | WO 2011/139973 A2 | 11/2011 | |

OTHER PUBLICATIONS

Janeway et al., Immunobiology, 3rd edition, Garland Publishing, Inc., 1997, pp. 3:1-3:11.*
International Search Report dated Jun. 9, 2015, in PCT/JP2015/054704.
Bijnens et al., "Importance of the Hinge Region between α-Helix F and the Main Part of Serpins, Based upon Identification of the Epitope of Plasminogen Activator Inhibitor Type 1 Neutralizing Antibodies," The Journal of Biological Chemistry, Mar. 3, 2000, 275(9):6375-6380.
Ohba, Hiroyoshi, "Development of Antibody Drugs by Artificial Antibody Library," Kotai Iyaku no Saizensen, 2007, 157-169, with English translation.
International Preliminary Report on Patentability and Written Opinion dated Aug. 23, 2016, in PCT/JP2015/054704, with English translation.
Extended European Search Report dated Aug. 21, 2017, in EP application No. 15751458.

* cited by examiner

*Primary Examiner* — Michael Szperka
(74) *Attorney, Agent, or Firm* — Foley & Lardner LLP

(57) ABSTRACT

[Problem] To provide an anti-human PAI-1 antibody for preventing or treating pulmonary fibrosis by binding to active human PAI-1 and inhibiting effects mediated by the active human PAI-1.
[Means for Solution] The present inventors have investigated anti-PAI-1 antibodies and consequently have provided an anti-human PAI-1 antibody comprising a heavy chain variable region consisting of the amino acid sequence of amino acid numbers 1 to 118 of SEQ ID NO: 2 and a light chain variable region consisting of the amino acid sequence of amino acid numbers 1 to 108 of SEQ ID NO: 4.

18 Claims, 1 Drawing Sheet

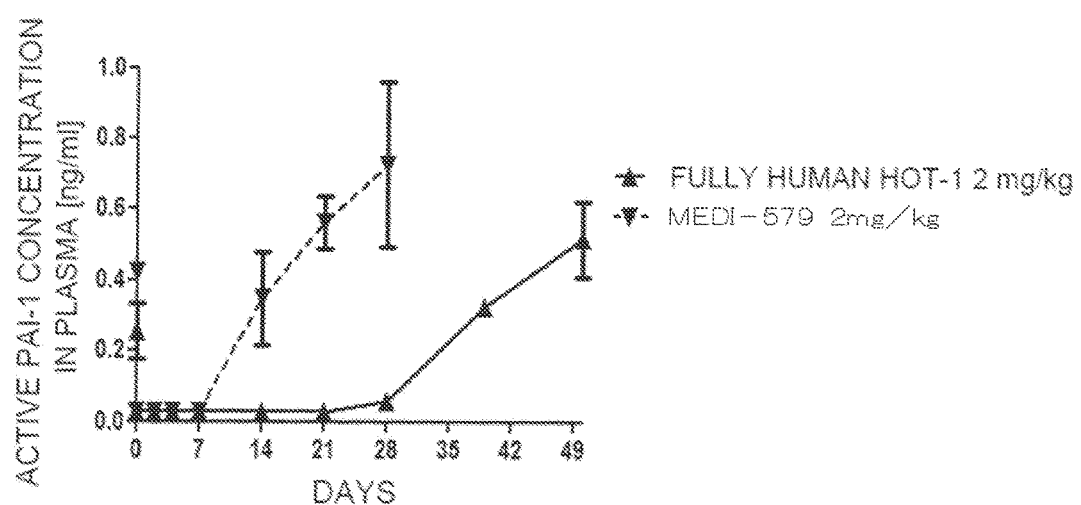

ANTI-HUMAN PAI-1 ANTIBODY

CROSS-REFERENCE TO RELATED APPLICATIONS

This application is a National Stage application of PCT/JP2015/054704, filed Feb. 20, 2015, which claims priority from Japanese application JP 2014-031319, filed Feb. 21, 2014.

TECHNICAL FIELD

The present invention relates to a novel anti-human PAI-1 antibody.

BACKGROUND ART

The plasminogen activator inhibitor-1 (PAI-1) is one of the serine protease inhibitors produced from the vascular endothelium or like. PAI-1 binds to a plasminogen activator (PA), which is a serine protease, to inactivate an enzymatic activity of PA (Mol. Cell. Endocrinol., 1990, Vol. 68, p. 1-19). With respect to PAI-1, there are active PAI-1, latent PAI-1, and PAI-1 bound to and complexed with PA, and the property of PAI-1 to inhibit PA is possessed only by active PAI-1 (Blood, 1987, Vol. 70, p. 1090-1098). There are two types of PA: tissue plasminogen activator (tPA) and urokinase-type plasminogen activator (uPA, also referred to as urokinase), both of which activate plasminogen to convert into plasmin, thereby catalyzing a reaction that lyses fibrin produced during blood clotting (hereinafter referred to as a fibrinolytic system). Active PAI-1 binds to tPA and uPA to form a complex. Biological properties that deactivate PA have been fully elucidated, and binding of active PAI-1 to PA results in inhibition of a fibrinolytic system to thereby facilitate thrombus formation.

The characteristic of the steric structure of active PAI-1 is that the active center loop which is a binding site to PA is extended and exposed to the outside of the protein (J. Biol. Chem., 2001, Vol. 276, p. 44912-44918). In circulating blood, active PAI-1 can bind to its cofactor vitronectin to form a complex (J. Biol. Chem., 1988, Vol. 263, p. 15454-15461). Vitronectin inhibits the conformational change of an active form of PAI-1 into a latent form thereof (J. Biol. Chem., 1990, Vol. 265, p. 18490-18498). Latent PAI-1 has a stable steric structure where the active center loop is folded inward. Once PAI-1 become a latent form, it becomes incapable of binding to PA (J. Biol. Chem., 2008, Vol. 283, p. 18147-18157. Nature, 1992, Vol. 355, p. 270-273). Moreover, since PAI-1 in complex with tPA or uPA is each bound to tPA or uPA, this PAI-1 cannot newly bind to another PA. That is, with respect to active PAI-1, there are active PAI-1 which is present as a monomer, and active PAI-1 which is present as a complex with vitronectin, and these active forms of PAI-1 have a function to inactivate PA by binding to PA.

An increase in active PAI-1 in the plasma has been suggested to be involved in tissue fibrosis and thrombus formation through the inhibition of PA, and is consequently believed to be involved in diseases, such as pulmonary fibrosis such as idiopathic pulmonary fibrosis, interstitial pneumonia, systemic lupus erythematosus, scleroderma, diabetic nephropathy, lupus nephritis, graft-versus-host disease, glomerulonephritis, nephrotic syndrome, renal fibrosis, chronic obstructive pulmonary disease, acute kidney injury, acute lung injury, acute respiratory failure, age-related macular degeneration, disseminated intravascular coagulation, post-surgical adhesion, symptomatic vitreomacular adhesion, diabetic retinopathy, arteriosclerosis, myocardial infarction, cerebral infarction, pulmonary infarction, ocular fibrosis-accompanying disease such as conjunctival scarring after glaucoma surgery, peritoneal sclerosis, and the like.

In association with pulmonary fibrosis, it has been reported that the expression and secretion of PAI-1 are increased in lung biopsy-derived fibroblasts of idiopathic pulmonary fibrosis patients (J. Biol. Chem., 2010, Vol. 285, No. 11, p. 8196-8206). In addition, it has been confirmed in tests using pathological model mice of bleomycin-induced pulmonary fibrosis that fibrosis of the lung is inhibited in mice with a genetic deficiency of PAI-1 (J. Clin. Invest., 1996, Vol. 97, No. 1, p. 232-237). Moreover, it has also been confirmed that fibrosis of the lung is inhibited by the inhibition of PAI-1, in the cases where a low molecular weight PAI-1 inhibitor and PAI-1 siRNA were administered to the above-mentioned pathological model mice (Arterioscler. Thromb. Vase. Biol., 2008, Vol. 28, p. 672-677. Thorax, 2010, Vol. 65, p. 334-340).

Therefore, the development of a monoclonal antibody having an activity capable of inhibiting the action by active PAI-1 through specific binding to active PAI-1 is expected to be useful in the prevention and treatment of various diseases where active PAI-1 is involved in the pathogenesis thereof.

As antibodies exhibiting a functional inhibitory action on active human PAI-1, there have been reported mouse monoclonal antibodies MA-33B8 (Patent Document 1), MA-33H1F7 (Non-Patent Document 1), MA-55F4C12 (Non-Patent Document 1), and MA-56A7C10 (Patent Document 2), and a humanized antibody CT140 of MA-33B8 (Patent Document 1), and a fully human antibody MEDI-579 (also referred to as CAT-1001 or PICK167_A01-fgl IgG1, Patent Document 3) which was prepared by using a phage. Among them, MA-56A7C10 and MEDI-579 exhibit about 4.0-fold and about 20-fold higher binding activity, respectively, for active human PAI-1 than for human PAI-1 having a steric structure other than the active form (Patent Documents 2 and 3). In addition, MEDI-579 also exhibits an inhibitory effect on mouse PAI-1, and is therefore expected to have a medicinal effect on lupus nephritis, scleroderma, diabetic nephropathy and thrombosis based on the experimental results using pathological model mice of those diseases (Patent Document 3).

In the case of using an anti-human PAI-1 antibody as an antibody drug, main factors defining an effective dose of the antibody may include an inhibitory activity of the antibody on the binding of active PAI-1 and PA, selectivity of the antibody for active PAI-1, and amounts of active PAI-1 and PAI-1 of other steric structures present in the body. As used herein, the term "PAI-1 of other steric structures" refers to latent PAI-1, and PAI-1 in complex with tPA or uPA.

More than 90% of total PAI-1 in human plasma is stored in platelets. About two thirds of total PAI-1 is an active form in the plasma except for platelets (Br. J. Haematol., 1988, Vol. 70, p. 327-333. Blood, 1988, Vol. 71, p. 220-225). Activity of PAI-1 in the plasma (activity of active PAI-1 expressed in terms of binding ability to tPA) as well as amounts of total PAI-1 in the plasma (total amounts of PAI-1 detected by an anti-PAI-1 antibody that detects all of PAI-1) and amounts of a complex of PAI-1 and tPA in the plasma (amounts of a complex that is detected as a combination of an anti-PAI-1 antibody and an anti-tPA antibody) are increased in various human pathologies (Thromb. Res., 2008, Vol. 122, p. 466-472. Arterioscler. Thromb. Vasc. Biol., 2000, Vol. 20, p. 2019-2023. Nat. Med., 1996, Vol. 2, p. 800-803). Also in the plasma except for platelets, the tPA-PAI-1 complex is present as about a third of the amount of active PAI-1 (Blood, 1990, Vol. 76, p. 930-937). uPA and uPA-PAI-1 complexes as well as tPA are present in tissues. In conclusion, PAI-1 other than active PAI-1 is present in the human body in an unignorable proportion in terms of total PAI-1 amount.

RELATED ART

Patent Document

[Patent Document 1] US 2010/0254979
[Patent Document 2] WO 2002/034776
[Patent Document 3] WO 2011/139973

Non-Patent Document

[Non-Patent Document 1] The Journal of Biological Chemistry (US) 2000, Vol. 275, p. 6375-6380

DISCLOSURE OF INVENTION

Problems to be Solved by the Invention

An object of the present invention is to provide an anti-human PAI-1 antibody for preventing or treating pulmonary fibrosis by more selectively inhibiting active human PAI-1 in comparison with a conventional anti-human PAI-1 antibody.

Means for Solving the Problems

The present inventors have extensively and repeatedly conducted inventive studies on the preparation of an anti-human PAI-1 antibody having high selectivity for active human PAI-1. As a consequence, the present inventors have prepared an anti-human PAI-1 antibody comprising a heavy chain variable region consisting of the amino acid sequence of amino acid numbers 1 to 118 of SEQ ID NO: 2 and a light chain variable region consisting of the amino acid sequence of amino acid numbers 1 to 108 of SEQ ID NO: 4 (Examples 1 to 3) and have found that this anti-human PAI-1 antibody inhibits active human PAT-1 in the plasma (Example 5) and has high selectivity for active human PAI-1 in complex with vitronectin (Example 6). The above-mentioned anti-human PAI-1 antibody has been provided and the present invention has been completed based on these results.

The present invention includes the following invention as a material or a method which is medically or industrially applicable.
(1) An anti-human PAI-1 antibody or an antigen-binding fragment thereof, comprising:
a heavy chain variable region comprising CDR1 consisting of the amino acid sequence of amino acid numbers 31 to 35 of SEQ ID NO: 2, CDR2 consisting of the amino acid sequence of amino acid numbers 50 to 66 of SEQ ID NO: 2, and CDR3 consisting of the amino acid sequence of amino acid numbers 99 to 107 of SEQ ID NO: 2; and
a light chain variable region comprising CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 97 of SEQ ID NO: 4.
(2) An anti-human PAI-1 antibody or an antigen-binding fragment thereof, which is selected from any one of the following 1) and 2):

1) an anti-human PAI-1 antibody or an antigen-binding fragment thereof, comprising a heavy chain variable region consisting of the amino acid sequence of amino acid numbers 1 to 118 of SEQ ID NO: 2, and a light chain variable region consisting of the amino acid sequence of amino acid numbers 1 to 108 of SEQ ID NO: 4; and
2) the anti-human PAI-1 antibody or the antigen-binding fragment thereof described in (1), which is an antibody or an antigen-binding fragment thereof derived from post-translational modification of the anti-human PAI-1 antibody or the antigen-binding fragment thereof of 1) above.
(3) The anti-human PAI-1 antibody or the antigen-binding fragment thereof described in (2), comprising a heavy chain variable region consisting of the amino acid sequence of amino acid numbers 1 to 118 of SEQ ID NO: 2, and a light chain variable region consisting of the amino acid sequence of amino acid numbers 1 to 108 of SEQ ID NO: 4.
(4) The anti-human PAI-1 antibody or the antigen-binding fragment thereof described in (2), which is an antibody or an antigen-binding fragment thereof derived from post-translational modification of an anti-human PAI-1 antibody or an antigen-binding fragment thereof comprising a heavy chain variable region consisting of the amino acid sequence of amino acid numbers 1 to 118 of SEQ ID NO: 2, and a light chain variable region consisting of the amino acid sequence of amino acid numbers 1 to 108 of SEQ ID NO: 4.
(5) The anti-human PAI-1 antibody or the antigen-binding fragment thereof described in (2) or (4), wherein the post-translational modification is pyroglutamylation at the N terminal of the heavy chain variable region and/or deletion of lysine at the C terminal of the heavy chain.
(6) The anti-human PAI-1 antibody or the antigen-binding fragment thereof described in any one of (1) to (5), comprising a heavy chain constant region which is a human Igγ1 constant region.
(7) The anti-human PAI-1 antibody or the antigen-binding fragment thereof described in any one of (1) to (5), comprising a light chain constant region which is a human Igκ constant region.
(8) The anti-human PAL-1 antibody or the antigen-binding fragment thereof described in any one of (1) to (5), comprising a heavy chain constant region which is a human Igγ1 constant region and a light chain constant region which is a human Igκ constant region.
(9) The anti-human PAI-1 antibody described in (3), comprising a heavy chain consisting of the amino acid sequence set forth in SEQ ID NO: 2 and a light chain consisting of the amino acid sequence set forth in SEQ ID NO: 4.
(10) The antigen-binding fragment described in any one of (1) to (8), which is a single-chain variable region fragment, Fab, Fab', or F(ab')$_2$.
(11) The anti-human PAI-1 antibody which is an antibody derived from post-translational modification of the anti-human PAI-1 antibody described in (9).
(12) The anti-human PAI-1 antibody described in (11), wherein the post-translational modification is pyroglutamylation at the N terminal of the heavy chain variable region and/or deletion of lysine at the C terminal of the heavy chain.
(13) The anti-human PAI-1 antibody described in (11), comprising a heavy chain consisting of the amino acid sequence of amino acid numbers 1 to 447 of SEQ ID NO: 2, and a light chain consisting of the amino acid sequence set forth in SEQ ID NO: 4.

(14) An anti-human PAI-1 antibody or an antigen-binding fragment thereof which inhibits the binding of the anti-human PAI-1 antibody described in (9) or (13) to active human PAI-1, binds to active human PAI-1 in complex with vitronectin, and does not bind to latent human PAI-1 and human PAI-1 in complex with a plasminogen activator.

(15) An anti-human PAL-1 antibody or an antigen-binding fragment thereof which binds to the same human PAI-1 epitope as the anti-human PAI-1 antibody described in (9) or (13).

(16) A polynucleotide comprising a base sequence encoding the heavy chain variable region of the anti-human PAI-1 antibody or the antigen-binding fragment thereof described in (3).

(17) A polynucleotide comprising a base sequence encoding the light chain variable region of the anti-human PAT-1 antibody or the antigen-binding fragment thereof described in (3).

(18) An expression vector comprising the polynucleotide described in (16) and/or (17).

(19) A host cell transformed with the expression vector described in (18), which is selected from the group consisting of the following (a) to (d):

(a) a host cell transformed with an expression vector comprising a polynucleotide comprising a base sequence encoding the heavy chain variable region of the anti-human PAI-1 antibody or the antigen-binding fragment thereof described in (3) and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human PAI-1 antibody or the antigen-binding fragment thereof described in (3) and an expression vector comprising a polynucleotide comprising a base sequence encoding the light chain variable region of the antibody or the antigen-binding fragment thereof;

(c) a host cell transformed with an expression vector comprising a polynucleotide comprising a base sequence encoding the heavy chain variable region of the anti-human PAI-1 antibody or the antigen-binding fragment thereof described in (3); and (d) a host cell transformed with an expression vector comprising a polynucleotide comprising a base sequence encoding the light chain variable region of the anti-human PAI-1 antibody or the antigen-binding fragment thereof described in (3).

(20) A host cell transformed with the expression vector described in (18), which is selected from the group consisting of the following (a) to (d):

(a) a host cell transformed with an expression vector comprising a polynucleotide comprising a base sequence encoding the heavy chain of the anti-human PAI-1 antibody described in (9) and a polynucleotide comprising a base sequence encoding the light chain of the antibody;

(b) a host cell transformed with an expression vector comprising a polynucleotide comprising a base sequence encoding the heavy chain of the anti-human PAI-1 antibody described in (9) and an expression vector comprising a polynucleotide comprising a base sequence encoding the light chain of the antibody;

(c) a host cell transformed with an expression vector comprising a polynucleotide comprising a base sequence encoding the heavy chain of the anti-human PAI-1 antibody described in (9); and (d) a host cell transformed with an expression vector comprising a polynucleotide comprising a base sequence encoding the light chain of the anti-human PAI-1 antibody described in (9).

(21) A method for producing an anti-human PAI-1 antibody or an antigen-binding fragment thereof, comprising culturing host cell(s) selected from the group consisting of the following (a) to (c) to express the anti-human PAI-1 antibody or the antigen-binding fragment thereof:

(a) a host cell transformed with an expression vector comprising a polynucleotide comprising a base sequence encoding the heavy chain variable region of the anti-human PAI-1 antibody or the antigen-binding fragment thereof described in (3) and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human PAI-1 antibody or the antigen-binding fragment thereof described in (3) and an expression vector comprising a polynucleotide comprising a base sequence encoding the light chain variable region of the antibody or the antigen-binding fragment thereof; and (c) a host cell transformed with an expression vector comprising a polynucleotide comprising a base sequence encoding the heavy chain variable region of the anti-human PAI-1 antibody or the antigen-binding fragment thereof described in (3), and a host cell transformed with an expression vector comprising a polynucleotide comprising a base sequence encoding the light chain variable region of the antibody or the antigen-binding fragment thereof.

(22) A method for producing an anti-human PAI-1 antibody, comprising culturing host cell(s) selected from the group consisting of the following (a) to (c) to express the anti-human PAI-1 antibody:

(a) a host cell transformed with an expression vector comprising a polynucleotide comprising a base sequence encoding the heavy chain of the anti-human PAI-1 antibody described in (9) and a polynucleotide comprising a base sequence encoding the light chain of the antibody;

(b) a host cell transformed with an expression vector comprising a polynucleotide comprising a base sequence encoding the heavy chain of the anti-human PAI-1 antibody described in (9) and an expression vector comprising a polynucleotide comprising a base sequence encoding the light chain of the antibody; and (c) a host cell transformed with an expression vector comprising a polynucleotide comprising a base sequence encoding the heavy chain of the anti-human PAI-1 antibody described in (9), and a host cell transformed with an expression vector comprising a polynucleotide comprising a base sequence encoding the light chain of the anti-human PAI-1 antibody.

(23) An anti-human PAI-1 antibody or an antigen-binding fragment thereof produced by the method described in (21).

(24) An anti-human PAI-1 antibody produced by the method described in (22).

(25) A pharmaceutical composition comprising the anti-human PAI-1 antibody or the antigen-binding fragment thereof described in any one of (1) to (15), (23) and (24), and a pharmaceutically acceptable excipient.

(26) A pharmaceutical composition comprising the anti-human PAL-1 antibody or the antigen-binding fragment thereof described in (3), the anti-human PAI-1 antibody or the antigen-binding fragment thereof described in (4), and a pharmaceutically acceptable excipient.
(27) A pharmaceutical composition comprising the anti-human PAI-1 antibody described in (9), the anti-human PAI-1 antibody described in (13), and a pharmaceutically acceptable excipient.
(28) The pharmaceutical composition described in any one of (25) to (27), which is a pharmaceutical composition for preventing or treating pulmonary fibrosis.
(29) The pharmaceutical composition described in (28), wherein pulmonary fibrosis is idiopathic pulmonary fibrosis.
(30) A method for preventing or treating pulmonary fibrosis, comprising administering a therapeutically effective amount of the anti-human PAI-1 antibody or the antigen-binding fragment thereof described in any one of (1) to (15), (23) and (24).
(31) The method described in (30), wherein pulmonary fibrosis is idiopathic pulmonary fibrosis.
(32) The anti-human PAI-1 antibody or the antigen-binding fragment thereof described in any one of (1) to (15), (23) and (24) for use in preventing or treating pulmonary fibrosis.
(33) The use described in (32), wherein pulmonary fibrosis is idiopathic pulmonary fibrosis.
(34) Use of the anti-human PAI-1 antibody or the antigen-binding fragment thereof described in any one of (1) to (15), (23) and (24) for manufacture of a pharmaceutical composition for preventing or treating pulmonary fibrosis.
(35) The use described in (34), wherein pulmonary fibrosis is idiopathic pulmonary fibrosis.

The anti-human PAI-1 antibody or an antigen-binding fragment thereof includes a fusion of the antibody or the antigen-binding fragment thereof with another peptide or protein, and a modification having a modifying agent bound thereto.

Effects of the Invention

The anti-human PAI-1 antibody of the present invention can be used as an agent for preventing or treating a disease where active human PAI-1 is involved in the pathogenesis thereof, for example, pulmonary fibrosis such as idiopathic pulmonary fibrosis, by inhibiting the function of active human PAI-1.

BRIEF DESCRIPTION OF THE DRAWINGS

FIG. 1 shows an inhibitory effect of fully human HOT-1 on active PAI-1 in monkey blood. The vertical axis indicates a concentration of active PAI-1 in the plasma.

EMBODIMENTS FOR CARRYING OUT THE INVENTION

Hereinafter, the present invention will be described in detail.

There are five classes of IgG, IgM, IgA, IgD, and IgE in an antibody. The basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, Igδ, and Igε corresponding to IgG, IgM, IgA, IgD, and IgE, respectively. Further, four subclasses of IgG1, IgG2, IgG3, and IgG4 are present in IgG, and the heavy chains respectively corresponding thereto are referred to as Igγ1, Igγ2, Igγ3, and Igγ4. Light chain usually consists of a polypeptide chain comprising 220 amino acids, two types of which, type L and type K are known, and are referred to as Igλ and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain. The respective antibody molecules typically consist of two identical light chains and two identical heavy chains.

With regard to intrachain S—S bonds, four of the S—S bonds are present in the heavy chain (five in Igμ and Igε) and two of them are present in the light chain; one loop is formed per 100 to 110 amino acid residues, and this steric structure is similar among the loops and are referred to as a structural unit or a domain. The domain located at the N terminal side in both of the heavy chain and the light chain, whose amino acid sequence is not constant even in a case of a sample from the same class (sub class) of the same kind of animal is referred to as a variable region, and respective domains are referred to as a heavy chain variable region ($V_H$) and a light chain variable region ($V_L$). The amino acid sequence of the C terminal side from the variable region is nearly constant in each class or subclass and is referred to as a constant region (each of the domains is called $C_H1$, $C_H2$, $C_H3$ and $C_L$, respectively).

An antigenic determinant site of an antibody is configured of $V_H$ and $V_L$, and the binding specificity depends on the amino acid sequence of this site. On the other hand, biological activities such as binding to complements and various Fc receptor expressing cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

Further, various kinds of antigen-binding fragments comprising $V_H$ and $V_L$ of an antibody have antigen binding activity. For example, a single-chain variable region fragment (scFv), Fab, Fab', and F(ab')$_2$ are exemplified as typical antigen-binding fragments. A Fab is a monovalent antigen-binding fragment which is constituted with a light-chain and a heavy-chain fragment including a $V_H$, a $C_H1$, and a portion of the hinge region. A Fab' is a monovalent antigen-binding fragment which is constituted with a light-chain and a heavy-chain fragment including a $V_H$, a $C_H1$, and a portion of the hinge region, and cysteine residues constituting the inter-heavy-chain S—S bond are included in the portion of the hinge region. A F(ab')$_2$ fragment is a bivalent antigen-binding fragment in which two Fab' fragments bind to each other via the inter-heavy-chain S—S bond in the hinge region. An scFv is a monovalent antigen-binding fragment which is constituted with a $V_H$ and $V_L$ connected with a linker.

<Anti-Human PAI-1 Antibody of the Present Invention>

The anti-human PAI-1 antibody or the antigen-binding fragment thereof of the present invention includes an anti-human PAI-1 antibody or an antigen-binding fragment thereof, having the following characteristics:

An anti-human PAI-1 antibody or an antigen-binding fragment thereof, comprising a heavy chain variable region consisting of the amino acid sequence of amino acid numbers 1 to 118 of SEQ ID NO: 2 and a light chain variable region consisting of the amino acid sequence of amino acid numbers 1 to 108 of SEQ ID NO: 4.

Preferably, the anti-human PAI-1 antibody or the antigen-binding fragment thereof of the present invention has the above characteristics and further comprises a heavy chain constant region and a light chain constant region. As the constant region, any subclasses of constant region (for example, a constant region of Igγ1, Igγ2, Igγ3, or Igγ4 as the heavy chain constant region and a constant region of Igλ, or Igκ as the light chain constant region) can be selected, but a human Igγ1 constant region is preferable as the heavy chain constant region.

A human Igγ1 constant region includes, for example, human Igγ1 constant region consisting of the amino acid sequence of amino acid numbers 119 to 448 of SEQ ID NO: 2.

A human Igκ constant region is preferable as a light chain constant region

A human Igκ constant region includes, for example, human Igκ constant region consisting of the amino acid sequence of amino acid numbers 109 to 214 of SEQ ID NO: 4.

As the anti-human PAI-1 antibody or the antigen-binding fragment thereof of the present invention, the anti-human PAI-1 antibody or the antigen-binding fragment thereof, comprising the above heavy chain variable region and light chain variable region, in which the heavy chain constant region is the human Igγ1 constant region and the light chain constant region is the human Igκ constant region is further preferable.

In one embodiment, the antigen-binding fragment of the present invention is scFv, Fab, Fab', or F(ab')$_2$.

In one embodiment, the anti-human PAI-1 antibody of the present invention is an anti-human PAI-1 antibody comprising a heavy chain consisting of the amino acid sequence shown by SEQ ID NO: 2 and a light chain consisting of the amino acid sequence shown by SEQ ID NO: 4.

It is known that when an antibody is expressed in cells, the antibody is modified after translation. Examples of the post-translational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such post-translational modifications occur in various antibodies (Journal of Pharmaceutical Sciences, 2008, Vol. 97, p. 2426-2447).

The anti-human PAI-1 antibody or the antigen-binding fragment thereof of the present invention includes an anti-human PAI-1 antibody or an antigen-binding fragment thereof derived from post-translational modification. Examples of the anti-human PAI-1 antibody or the antigen-binding fragment thereof of the present invention, which is derived from post-translational modification, include anti-human PAI-1 antibodies or antigen-binding fragments thereof, which have undergone pyroglutamylation at the N terminal of the heavy chain variable region and/or deletion of lysine at the C terminal of the heavy chain. It is known in the field that such post-translational modification due to pyroglutamylation at the N terminal and deletion of lysine at the C terminal does not have any influence on the activity of the antibody (Analytical Biochemistry, 2006, Vol. 348, p. 24-39).

In one embodiment, the anti-human PAI-1 antibody of the present invention is an anti-human PAI-1 antibody having the following characteristics.

An anti-human PAI-1 antibody comprising a heavy chain consisting of the amino acid sequence of SEQ ID NO: 2 in which glutamic acid of the amino acid number 1 is modified to pyroglutamic acid and/or lysine of the amino acid number 448 is deleted in SEQ ID NO: 2 and a light chain consisting of the amino acid sequence shown by SEQ ID NO: 4.

In another embodiment, the anti-human PAI-1 antibody of the present invention is an anti-human PAI-1 antibody having the following characteristics.

The anti-human PAI-1 antibody comprising a heavy chain consisting of the amino acid sequence of amino acid numbers 1 to 447 of SEQ ID NO: 2 and a light chain consisting of the amino acid sequence shown by SEQ ID NO: 4.

The present invention includes an anti-human PAI-1 antibody or an antigen-binding fragment thereof, having the following characteristics.

An anti-human PAI-1 antibody or an antigen-binding fragment thereof, comprising a heavy chain variable region comprising CDR1 consisting of the amino acid sequence of amino acid numbers 31 to 35 of SEQ ID NO: 2, CDR2 consisting of the amino acid sequence of amino acid numbers 50 to 66 of SEQ ID NO: 2, and CDR3 consisting of the amino acid sequence of amino acid numbers 99 to 107 of SEQ ID NO: 2, and a light chain variable region comprising CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 97 of SEQ ID NO: 4.

The anti-human PAI-1 antibody or the antigen-binding fragment thereof of the present invention is an antibody that binds to active human PAI-1 in complex with vitronectin (also referred to as VTN-PAI-1 complex). Examples of active human PAI-1 present in the body include active human PAI-1 which is present as a monomer, and a VTN-PAI-1 complex. With regard to the VTN-PAI-1 complex among them, the conformational change from the active form of human PAI-1 to the latent form thereof is inhibited by binding of PAI-1 to vitronectin, whereby the structure of active human PAI-1 is more stably held than active human PAI-1 which is present as a monomer. In addition, the active center loop structure of active human PAI-1 is not affected in the VTN-PAI-1 complex (Nat. Struct. Biol., 2003, Vol. 10, p. 541-544). Thus, the selectivity of an antibody for active human PAI-1 can be more precisely estimated by evaluating the binding activity of the anti-human PAI-1 antibody for the VTN-PAI-1 complex.

Further, the anti-human PAI-1 antibody or the antigen-binding fragment thereof of the present invention also includes an antibody that also binds to active human PAI-1 which is present as a monomer, as well as to a VTN-PAI-1 complex.

Whether or not such an antibody binds to a VTN-PAI-1 complex or active PAI-1 which is present as a monomer may be confirmed by using a known method of measuring a binding activity. Examples of the method of measuring a binding activity include Enzyme-Linked ImmunoSorbent Assay (ELISA) and surface plasmon resonance (SPR). In the case of using ELISA, in an exemplary method, vitronectin (BD Biosciences, 354238) is immobilized, followed by blocking, and then recombinant active human PAI-1 (Molecular Innovations Inc., PAI-A) is immobilized to thereby immobilize a VTN-PAI-1 complex. A test antibody is added and reacted therewith. This is followed by the reaction with a secondary antibody such as an anti-IgG antibody labeled with horseradish peroxidase (HRP) or the like, washing, and then activity measurement using an activity detection reagent (for example, in the case of HRP labeling, a peroxidase color development kit (Sumitomo Bakelite Co., Ltd.)) or the like, whereby it is possible to confirm whether or not the test antibody binds to the VTN-PAI-1 complex. In the case of using SPR, for example, Biacore (registered trademark) T200 (GE Healthcare Japan) may be used. In an exemplary method, a test antibody is immobilized on the surface of a sensor chip, and recombinant active human PAI-1 (Molecular Innovations Inc., PAI-A) is added to a flow path. Whether or not the test antibody binds to active human PAI-1 which is present as a monomer can be confirmed by analyzing an association rate constant (ka), a dissociation rate constant (kd), and a dissociation constant (KD) of the antibody and active human PAI-1.

Preferably, the anti-human PAL-1 antibody or the antigen-binding fragment thereof of the present invention is an antibody which binds to a VTN-PAI-1 complex and has an inhibitory activity on active human PAI-1 in the plasma. More preferably, the anti-human PAI-1 antibody or the antigen-binding fragment thereof of the present invention is an antibody which binds to a VTN-PAI-1 complex, has an inhibitory activity on active human PAI-1 in the plasma, and does not bind to latent human PAI-1 and human PAI-1 in complex with PA. The method as described in Example 5 below may be used as a method for specifically evaluating an inhibitory activity on active human PAI-1 in the plasma.

The phrase "does not bind to latent human PAI-1" refers to an EC50 value (ng/mL) >10,000 in the case of evaluating the binding activity of an antibody for latent human PAI-1, and the term "EC50 value (ng/mL) >10,000" means that an antibody concentration that exhibits 50% of the maximum activity mean is greater than 10,000 ng/mL. The method used for this evaluation is as shown below.

(Evaluation of Binding Activity for Latent Human PAI-1)

Recombinant latent human PAI-1 (Molecular Innovations Inc., PAI-L) is diluted to 1000 ng/mL in phosphate-buffered saline (PBS), and added at 100 μL/well to a Nunc MaxiSorp clear 96-well plate (Nunc Inc.) which is then allowed to stand overnight at 4° C. to immobilize the latent human PAI-1. The coating solution is removed by reverse centrifugation, and a blocking agent (Thermo Scientific, 37532) is added at 200 μL/well, followed by allowing to stand at room temperature for 30 minutes. The plate is washed with a washing solution (Tris-buffered saline (TBS) containing 0.05% Tween-20), and a test antibody, which was diluted in eight steps in a range from 100,000 ng/mL to 0.01 ng/mL with PBS containing 0.1% bovine serum-derived albumin (BSA), is added at 100 μL/well, followed by allowing to stand at room temperature for 30 minutes. Each of MEDI-579 (Patent Document 3) as a comparative antibody in the case where the test antibody has a human Fc region, and MA-56A7C10 (Hycult Biotech Inc., HM2182) as a comparative antibody in the case where the test antibody has a mouse Fc region is diluted in seven steps in a range from 10,000 ng/mL to 0.01 ng/mL with 0.1% BSA-containing PBS, and then added to the wells. A well to which 0.1% BSA-containing PBS was added instead of a test antibody is prepared as a control. After washing three times with a washing solution, a detection antibody diluted 2,000-fold using a blocking agent (NACALAI TESQUE, INC., 03953-95) solution which was diluted 20-fold in PBS is added at 100 μL/well, followed by the reaction. An HRP-labeled goat anti-mouse Ig antibody (Southern Biotech, 1010-05) for the detection of a test antibody having an Fc region of a mouse antibody and an HRP-labeled rabbit anti-human Ig antibody (Southern Biotech, 6145-05) for the detection of a test antibody having an Fc region of a human antibody are used as the detection antibody. After incubation at room temperature for 30 minutes, the plates are washed three times with a washing solution. A color developing solution contained in a peroxidase color development kit (Sumitomo Bakelite Co., Ltd.) is added at 100 μL/well, followed by allowing to stand at room temperature for about 15 minutes, 100 μL of a reaction stop solution contained in the color development kit is added, and then the OD450 value is measured using an EnVision counter (PerkinElmer Co., Ltd.). In connection with the calculation of a PAI-1 binding rate at each concentration of a test antibody, the measurement value of the well to which 0.1% BSA-containing PBS was added instead of a test antibody is taken to be 0%, and the measurement value at the maximum concentration of a test antibody is set to 100%. Meanwhile, in the case where a test antibody has a human Fc region, the measurement value of the maximum concentration of MEDI-579 in an evaluation system is set to 100% when a test antibody is added at the maximum concentration (100,000 ng/mL) but the measurement value does not reach the measurement value of the maximum concentration (10,000 ng/mL) of MEDI-579 in the evaluation system. In the case where a test antibody has a mouse Fc region, the measurement value of the maximum concentration of MA-56A7C10 in an evaluation system is set to 100% when a test antibody is added at the maximum concentration (100,000 ng/mL) but the measurement value does not reach the measurement value of the maximum concentration (10,000 ng/mL) of MA-56A7C10 in the evaluation system. The calculated PAI-1 binding rate is analyzed, and an EC50 value of the test antibody is calculated by four-parameter logistic curve regression.

The phrase "does not bind to human PAI-1 in complex with a plasminogen activator" refers to an EC50 value (ng/mL) >10,000 for each complex in the case of evaluating the binding activity of an antibody for human PAI-1 in complex with uPA or tPA which is a plasminogen activator (PA) (each of which is referred to as uPA-PAI-1 complex and tPA-PAI-1 complex), and the term "EC50 value (ng/mL) >10,000" means that an antibody concentration that exhibits 50% of the maximum activity is greater than 10,000 ng/mL. The method used for this evaluation is as shown below.

(Evaluation of Binding Activity for uPA-PAI-1 Complex)

uPA (intravenous urokinase $6 \times 10^4$ units "Benesis (registered trademark)"; Mitsubishi Tanabe Pharma Corporation) is diluted to 100 units/mL in PBS, and added at 100 μL/well to a Nunc MaxiSorp clear 96-well plate (Nunc Inc.) which is then allowed to stand overnight at 4° C. to immobilize the uPA. The coating solution is removed by reverse centrifugation, and a blocking agent (Thermo Scientific, 37532) is added at 200 μL/well, followed by allowing to stand at room temperature for 30 minutes. Recombinant active human PAI-1 (Molecular Innovations Inc., PAI-A) diluted to 1000 ng/mL in 0.1% BSA-containing PBS is added at 100 μL/well and allowed to be captured on the uPA. The plate is washed with a washing solution (0.05% Tween-20-containing TBS), and a test antibody, which was diluted in eight steps in a range from 100,000 ng/mL to 0.01 ng/mL with 0.1% BSA-containing PBS, is added at 100 μL/well, followed by allowing to stand at room temperature for 30 minutes. Each of MEDI-579 (Patent Document 3) as a comparative antibody in the case where the test antibody has a human Fc region, and MA-56A7C10 (Hycult Biotech Inc., HM2182) as a comparative antibody in the case where the test antibody has a mouse Fc region is diluted in seven steps in a range from 10,000 ng/mL to 0.01 ng/mL with 0.1% BSA-containing PBS, and then added to the wells. A well to which 0.1% BSA-containing PBS was added instead of a test antibody is prepared as a control. After washing three times with a washing solution, a detection antibody diluted 2,000-fold using a blocking agent (NACALAI TESQUE, INC., 03953-95) solution which was diluted 20-fold in PBS is added at 100 μL/well, followed by the reaction. An HRP-labeled goat anti-mouse Ig antibody (Southern Biotech, 1010-05) for the detection of a test antibody having an Fc region of a mouse antibody and an HRP-labeled rabbit anti-human Ig antibody (Southern Biotech, 6145-05) for the detection of a test antibody having an Fc region of a human antibody are used as the detection antibody. After incubation at room temperature for 30 minutes, the plates are washed three times with a washing solution. A color developing solution contained in a peroxidase color development kit (Sumitomo Bakelite Co., Ltd.) is added at 100 μL/well, followed by allowing to stand at room temperature for about 15 minutes, 100 μL of a reaction stop solution contained in the color development kit is added, and then the OD450 value is measured using an EnVision counter (PerkinElmer Co., Ltd.). In connection with the calculation of a PAI-1 binding rate at each concentration of a test antibody, the measurement value of the well to which 0.1% BSA-containing PBS was added instead of a test antibody is taken to be 0%, and the measurement value at the maximum concentration of a test antibody is set to 100%. Meanwhile, in the case where a test antibody has a human Fc region, the measurement value of the maximum concentration of MEDI-579 in an evaluation system is set to 100% when a test antibody is added at the maximum concentration (100,000 ng/mL) but the measurement value does not reach the measurement value of the maximum concentration (10,000 ng/mL) of MEDI-579 in the evaluation system. In the case where a test antibody has a mouse Fc region, the measurement value of the maximum concentration of MA-56A7C10 in an evaluation system is set to 100% when a test antibody is added at the maximum concentration (100,000 ng/mL) but the measurement value does not reach the measurement value of the maximum concentration (10,000 ng/mL) of MA-56A7C10 in the evaluation system. The calculated PAI-1 binding rate is analyzed, and an EC50 value of the test antibody is calculated by four-parameter logistic curve regression.

(Evaluation of Binding Activity for tPA-PAI-1 Complex)

tPA (Activacin (registered trademark) for Injection 6,000,000; Kyowa Hakko Kirin Co., Ltd.) is diluted to 1000 units/mL in PBS, and added at 100 μL/well to a Nunc MaxiSorp clear 96-well plate (Nunc Inc.) which is then allowed to stand overnight at 4° C. to immobilize the tPA. The coating solution is removed by reverse centrifugation, and a blocking agent (Thermo Scientific, 37532) is added at 200 μL/well, followed by allowing to stand at room temperature for 30 minutes. Recombinant active human PAI-1 (Molecular Innovations Inc., PAI-A) diluted to 1000 ng/mL in 0.1% BSA-containing PBS is added at 100 μL/well and allowed to be captured on the tPA. The plate is washed with a washing solution (0.05% Tween-20-containing TBS), and a test antibody, which was diluted in eight steps in a range from 100,000 ng/mL to 0.01 ng/mL with 0.1% BSA-containing PBS, is added at 100 μL/well, followed by allowing to stand at room temperature for 30 minutes. Each of MEDI-579 (Patent Document 3) as a comparative antibody in the case where the test antibody has a human Fc region, and MA-56A7C10 (Hycult Biotech Inc., HM2182) as a comparative antibody in the case where the test antibody has a mouse Fc region is diluted in seven steps in a range from 10,000 ng/mL to 0.01 ng/mL with 0.1% BSA-containing PBS, and then added to the wells. As a control, a well to which 0.1% BSA-containing PBS was added instead of a test antibody is prepared. After washing three times with a washing solution, a detection antibody diluted 2,000-fold using a blocking agent (NACALAI TESQUE, INC., 03953-95) solution which was diluted 20-fold in PBS is added at 100 μL/well, followed by the reaction. An HRP-labeled goat anti-mouse Ig antibody (Southern Biotech, 1010-05) for the detection of a test antibody having an Fc region of a mouse antibody and an HRP-labeled rabbit anti-human Ig antibody (Southern Biotech, 6145-05) for the detection of a test antibody having an Fc region of a human antibody are used as the detection antibody. After incubation at room temperature for 30 minutes, the plates are washed three times with a washing solution. A color developing solution contained in a peroxidase color development kit (Sumitomo Bakelite Co., Ltd.) is added at 100 μL/well, followed by allowing to stand at room temperature for about 15 minutes, 100 μL of a reaction stop solution contained in the color development kit is added, and then the OD450 value is measured using an EnVision counter (PerkinElmer Co., Ltd.). In connection with the calculation of a PAI-1 binding rate at each concentration of a test antibody, the measurement value of the well to which 0.1% BSA-containing PBS was added instead of a test antibody is taken to be 0%, and the measurement value at the maximum concentration of a test antibody is set to 100%. Meanwhile, in the case where a test antibody has a human Fc region, the measurement value of the maximum concentration of MEDI-579 in an evaluation system is set to 100% when a test antibody is added at the maximum concentration (100,000 ng/mL) but the measurement value does not reach the measurement value of the maximum concentration (10,000 ng/mL) of MEDI-579 in the evaluation system. In the case where a test antibody has a mouse Fc region, the measurement value of the maximum concentration of MA-56A7C10 in an evaluation system is set to 100% when a test antibody is added at the maximum concentration (100,000 ng/mL) but the measurement value does not reach the measurement value of the maximum concentration (10,000 ng/mL) of MA-56A7C10 in the evaluation system. The calculated PAI-1 binding rate is analyzed, and an EC50 value of the test antibody is calculated by four-parameter logistic curve regression.

The anti-human PAI-1 antibody or the antigen-binding fragment thereof of the present invention also includes an anti-human PAI-1 antibody or an antigen-binding fragment thereof which inhibits the binding of an anti-human PAI-1 antibody comprising a heavy chain consisting of the amino acid sequence set forth in SEQ ID NO: 2 and a light chain consisting of the amino acid sequence set forth in SEQ ID NO: 4 or an anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4 to active human PAI-1, binds to active human PAI-1 in complex with vitronectin, and does not bind to latent human PAI-1 and human PAI-1 in complex with a plasminogen activator.

Whether or not a test antibody inhibits the binding of an anti-human PAI-1 antibody comprising a heavy chain consisting of the amino acid sequence set forth in SEQ ID NO: 2 and a light chain consisting of the amino acid sequence set forth in SEQ ID NO: 4 or an anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4 to active human PAI-1 can be confirmed using the following method. Vitronectin (BD Biosciences, 354238) is immobilized, followed by blocking, and then active human PAI-1 (Molecular Innovations Inc., PAI-A) is immobilized to thereby immobilize a VTN-PAI-1 complex. A test antibody is added and reacted therewith. This is followed by the reaction with a secondary antibody of an anti-human PAI-1 antibody comprising a heavy chain consisting of the amino acid sequence set forth in SEQ ID NO: 2 and a light chain consisting of the amino acid sequence set forth in SEQ ID NO: 4 or an anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4, which has been labeled with HRP or the like, washing, and then activity measurement using an activity detection reagent (for example, in the case of HRP labeling, a peroxidase color development kit (Sumitomo Bakelite Co., Ltd.)) or the like. In the case where the binding activity of an anti-human PAI-1 antibody comprising a heavy chain consisting of the amino acid sequence set forth in SEQ ID NO: 2 and a light chain consisting of the amino acid sequence set forth in SEQ ID NO: 4 or an anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4 is significantly reduced by the addition of a test antibody, it can be determined that the test antibody inhibits the binding of an anti-human PAI-1 antibody comprising a heavy chain consisting of the amino acid sequence set forth in SEQ ID NO: 2 and a light chain consisting of the amino acid sequence set forth in SEQ ID NO: 4 or an anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4 to active human PAI-1.

The anti-human PAI-1 antibody or the antigen-binding fragment thereof of the present invention also includes an anti-human PAI-1 antibody or an antigen-binding fragment thereof which binds to the same human PAI-1 epitope as the anti-human PAI-1 antibody comprising a heavy chain consisting of the amino acid sequence set forth in SEQ ID NO: 2 and a light chain consisting of the amino acid sequence set forth in SEQ ID NO: 4 or the anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4. As used herein, the term "epitope" refers to an antigenic site which is recognized by an antibody.

Whether or not a test antibody binds to the same human PAI-1 epitope as the anti-human PAI-1 antibody comprising a heavy chain consisting of the amino acid sequence set forth in SEQ ID NO: 2 and a light chain consisting of the amino acid sequence set forth in SEQ ID NO: 4 or the anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4 can be confirmed by using a known epitope determination method. Examples of the method of determining an epitope include methods such as X-ray crystal structure analysis and ELISA. In the case of using ELISA, in an exemplary method, a human PAI-1 partial peptide is immobilized, and a test antibody is added and reacted therewith. This is followed by the reaction with a secondary antibody such as an anti-IgG antibody labeled with HRP or the like, washing, and then activity measurement using an activity detection reagent (for example, in the case of HRP labeling, a peroxidase color development kit (Sumitomo Bakelite Co., Ltd.)) or the like, whereby it is possible to confirm whether or not the test antibody binds to the human PAI-1 partial peptide. The epitope of the test antibody can be determined by evaluating the binding activity to human PAI-1 partial peptides having different amino acid sequences. In the case where the epitope of the test antibody is the same as the epitope of an anti-human PAI-1 antibody comprising a heavy chain consisting of the amino acid sequence set forth in SEQ ID NO: 2 and a light chain consisting of the amino acid sequence set forth in SEQ ID NO: 4 or an anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4, it can be determined that the test antibody binds to the same human PAI-1 epitope as the anti-human PAI-1 antibody comprising a heavy chain consisting of the amino acid sequence set forth in SEQ ID NO: 2 and a light chain consisting of the amino acid sequence set forth in SEQ ID NO: 4 or the anti-human PAI-1 antibody comprising a heavy chain consisting of the amino acid sequence of amino acid numbers 1 to 447 of SEQ ID NO: 2 and a light chain consisting of the amino acid sequence set forth in SEQ ID NO: 4.

Further, the anti-human PAI-1 antibody of the present invention also includes an antibody which binds to active PAI-1 derived from other animals and in complex with vitronectin (for example, active monkey PAI-1 in complex with vitronectin) as well as to a VTN-PAI-1 complex, as long as it is an antibody that binds to the VTN-PAI-1 complex.

The anti-human PAI-1 antibody of the present invention can be easily prepared by a person skilled in the art using a known method in the field, based on sequence information on the heavy chain variable region and the light chain variable region of the antibody of the invention, which is disclosed in the present specification. The anti-human PAI-1 antibody of the present invention is not particularly limited, but can be produced according to the method described in the section of <Method of producing anti-human PAI-1 antibody of the present invention, and anti-human PAI-1 antibody produced by the method> described below.

The anti-human PAI-1 antibody of the present invention is further purified if desired and then formulated according to a conventional method, and may be used for the prevention or treatment of diseases where active PAI-1 is involved in the pathogenesis thereof, for example, pulmonary fibrosis such as idiopathic pulmonary fibrosis, interstitial pneumonia, systemic lupus erythematosus, scleroderma, diabetic nephropathy, lupus nephritis, graft-versus-host disease, glomerulonephritis, nephrotic syndrome, renal fibrosis, chronic obstructive pulmonary disease, acute kidney injury, acute lung injury, acute respiratory failure, age-related macular degeneration, disseminated intravascular coagulation, post-surgical adhesion, symptomatic vitreomacular adhesion, diabetic retinopathy, arteriosclerosis, myocardial infarction, cerebral infarction, pulmonary infarction, ocular fibrosis-accompanying disease such as conjunctival scarring after glaucoma surgery, peritoneal sclerosis, and diseases of the like.

<Polynucleotide of the Present Invention>

The polynucleotide of the present invention includes a polynucleotide comprising a base sequence encoding the heavy chain variable region of the anti-human PAI-1 antibody or the antigen-binding fragment thereof of the present invention and a polynucleotide comprising a base sequence encoding the light chain variable region of the anti-human PAI-1 antibody or the antigen-binding fragment thereof of the present invention.

In one embodiment, the polynucleotide comprising a base sequence encoding the heavy chain variable region of the anti-human PAI-1 antibody or the antigen-binding fragment thereof of the present invention is a polynucleotide comprising a base sequence encoding the heavy chain variable region consisting of the amino acid sequence of amino acid numbers 1 to 118 of SEQ ID NO: 2.

The polynucleotide comprising the base sequence encoding the heavy chain variable region shown by the amino acid sequence of amino acid numbers 1 to 118 of SEQ ID NO: 2 includes, for example, a polynucleotide comprising the base sequence of the base numbers 1 to 354 of SEQ ID NO: 1.

In a preferred embodiment, the polynucleotide comprising a base sequence encoding the heavy chain variable region of the anti-human PAI-1 antibody of the present invention is a polynucleotide comprising the base sequence encoding the heavy chain consisting of the amino acid sequence shown by SEQ ID NO: 2.

Examples of the polynucleotide comprising the base sequence encoding the heavy chain consisting of the amino acid sequence shown by SEQ ID NO: 2 include a polynucleotide comprising the base sequence shown by SEQ ID NO: 1.

In one embodiment, the polynucleotide comprising the base sequence encoding the light chain variable region of the anti-human PAI-1 antibody or the antigen-binding fragment thereof of the present invention is a polynucleotide comprising a base sequence encoding the light chain variable region consisting of the amino acid sequence of amino acid numbers 1 to 108 of SEQ ID NO: 4.

Examples of the polynucleotide comprising the base sequence encoding the light chain variable region consisting of the amino acid sequence of amino acid numbers 1 to 108 of SEQ ID NO: 4 include a polynucleotide comprising a base sequence of the base numbers 1 to 324 of SEQ ID NO: 3.

In a preferred embodiment, the polynucleotide comprising the base sequence encoding the light chain variable region of the anti-human PAI-1 antibody of the present invention is a polynucleotide comprising a base sequence encoding the light chain consisting of the amino acid sequence shown by SEQ ID NO: 4.

Examples of the polynucleotide comprising the base sequence encoding the light chain consisting of the amino acid sequence shown by SEQ ID NO: 4 include a polynucleotide comprising the base sequence shown by SEQ ID NO: 3.

The polynucleotide of the present invention can be easily prepared by a person skilled in the art using a known method in the field based on the base sequence. For example, the polynucleotide of the present invention can be synthesized using a known gene synthesis method in the field. As the gene synthesis method, various methods known by a person skilled in the art such as a synthesis method of antibody genes described in WO90/07861 can be used.

<Expression Vector of the Present Invention>

An expression vector of the present invention includes an expression vector comprising the polynucleotide comprising the base sequence encoding the heavy chain variable region of the anti-human PAI-1 antibody or the antigen-binding fragment thereof of the present invention and/or the polynucleotide comprising the base sequence encoding the light chain variable region of the anti-human PAI-1 antibody or the antigen-binding fragment thereof of the present invention.

Preferred expression vectors of the present invention include an expression vector comprising a polynucleotide comprising the base sequence encoding the heavy chain of the anti-human PAI-1 antibody of the present invention, an expression vector comprising a polynucleotide comprising the base sequence encoding the light chain of the anti-human PAI-1 antibody of the present invention, or an expression vector comprising a polynucleotide comprising the base sequence encoding the heavy chain of the anti-human PAI-1 antibody of the present invention and a polynucleotide comprising the base sequence encoding the light chain of the antibody.

The expression vector used to express the polynucleotide of the present invention are not particularly limited as long as a polynucleotide comprising the base sequence encoding the heavy chain variable region of the anti-human PAI-1 antibody or the antigen-binding fragment thereof of the present invention and/or a polynucleotide comprising the base sequence encoding the light chain variable region of the anti-human PAI-1 antibody or the antigen-binding fragment thereof of the present invention can be expressed in various host cells of eukaryotic cells (for example, animal cells, insect cells, plant cells, and yeast) and/or prokaryotic cells (for example, *Escherichia coli*), and the polypeptides encoded by these can be produced. Examples of the expression vector include plasmid vectors, viral vectors (for example, adenovirus or retrovirus), and the like. Preferably pEE6.4 or pEE12.4 (Lonza, Inc.) can be used. Further, antibody genes can be expressed by transferring a variable region gene fragment to expression vectors comprising human Ig constant region genes in advance such as AG-γ1 or AG-K (for example, see WO94/20632).

The expression vector of the present invention may include a promoter that is operably linked to the polynucleotide of the present invention. Examples of the promoter for expressing the polynucleotide of the invention with animal cells include a virus-derived promoter such as CMV, RSV, or SV40, an actin promoter, an EF (elongation factor) 1α promoter, and a heat shock promoter. Examples of promoters for expression by bacteria (for example, *Escherichia*) include a trp promoter, a lac promoter, a λPL promoter, and a tac promoter. Further, examples of promoters for expression by yeast include a GAL1 promoter, a GAL10 promoter, a PH05 promoter, a PGK promoter, a GAP promoter, and an ADH promoter.

In the case of using an animal cell, an insect cell, or yeast as the host cell, the expression vector of the present invention may comprise start codon and stop codon. In this case, the expression vector of the present invention may comprise an enhancer sequence, an untranslated region on the 5' side and the 3' side of genes encoding the antibody of the present invention or the heavy chain variable region or the light chain variable region, a secretory signal sequence, a splicing junction, a polyadenylation site, or a replicable unit. When *Escherichia coli* is used as the host cell, the expression vector of the present invention may comprise a start codon, a stop codon, a terminator region, and a replicon. In this case, the expression vector of the present invention may comprise a selection marker (for example, tetracycline resistant genes, ampicillin resistant genes, kanamycin resistant genes, neomycin resistant genes, or dihydrofolate reductase genes) which is generally used according to the necessity.

<Transformed Host Cell of the Present Invention>

The transformed host cell of the present invention includes a host cell transformed with the expression vector of the present invention which is selected from the group consisting of the following (a) to (d):

(a) a host cell transformed with an expression vector comprising the polynucleotide comprising the base sequence encoding the heavy chain variable region of the anti-human PAI-1 antibody or the antigen-binding fragment thereof of the present invention and the polynucleotide comprising the base sequence encoding the light chain variable region of the antibody or the antigen-binding fragment thereof;

(b) a host cell transformed with an expression vector comprising the polynucleotide comprising the base sequence encoding the heavy chain variable region of the anti-human PAL-1 antibody or the antigen-binding fragment thereof of the present invention and an expression vector comprising the polynucleotide comprising the base sequence encoding the light chain variable region of the antibody or the antigen-binding fragment thereof;

(c) a host cell transformed with an expression vector comprising the polynucleotide comprising the base sequence encoding the heavy chain variable region of the anti-human PAI-1 antibody or the antigen-binding fragment thereof of the present invention; and (d) a host cell transformed with an expression vector comprising the polynucleotide comprising the base sequence encoding the light chain variable region of the anti-human PAI-1 antibody or the antigen-binding fragment thereof of the present invention.

In one embodiment, the transformed host cell of the present invention is a host cell transformed with the expression vector of the present invention which is selected from the group consisting of the following (a) to (d):

(a) a host cell transformed with an expression vector comprising a polynucleotide comprising the base sequence encoding the heavy chain of the anti-human PAI-1 antibody of the present invention and a polynucleotide comprising the base sequence encoding the light chain of the antibody;

(b) a host cell transformed with an expression vector comprising a polynucleotide comprising the base sequence encoding the heavy chain of the anti-human PAI-1 antibody of the present invention and an expression vector comprising a polynucleotide comprising the base sequence encoding the light chain of the antibody;

(c) a host cell transformed with an expression vector comprising a polynucleotide comprising the base sequence encoding the heavy chain of the anti-human PAI-1 antibody of the present invention; and (d) a host cell transformed with an expression vector comprising a polynucleotide comprising the base sequence encoding the light chain of the anti-human PAI-1 antibody of the present invention.

Preferred examples of the transformed host cell of the present invention include a host cell transformed with an expression vector comprising a polynucleotide comprising the base sequence encoding the heavy chain of the anti-human PAI-1 antibody of the present invention and a polynucleotide comprising the base sequence encoding the light chain of the antibody, and a host cell transformed with an expression vector comprising a polynucleotide comprising the base sequence encoding the heavy chain of the anti-human PAI-1 antibody of the present invention and an expression vector comprising a polynucleotide comprising the base sequence encoding the light chain of the antibody.

The transformed host cell is not particularly limited as long as the host cell is appropriate for the expression vector being used, transformed with the expression vector, and can express the antibody. Examples of the transformed host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) or the like). Preferably cultured cells such as CHO cells (such as CHO-K1 SV cells and CHO-DG 44 cells), 293 cells, or NS0 cells can be used.

A method of transforming the host cell is not particularly limited, but, for example, a calcium phosphate method or an electroporation method can be used.

<Method of Producing Anti-Human PAI-1 Antibody of the Present Invention, and Anti-Human PAI-1 Antibody Produced by the Method>

The method for producing the anti-human PAI-1 antibody or the antigen-binding fragment thereof of the present invention includes a method for producing an anti-human PAI-1 antibody or an antigen-binding fragment thereof, comprising culturing host cell(s) selected from the group consisting of the following (a) to (c) to express the anti-human PAI-1 antibody or the antigen-binding fragment thereof:

(a) a host cell transformed with an expression vector comprising a polynucleotide comprising a base sequence encoding the heavy chain variable region of the anti-human PAI-1 antibody or the antigen-binding fragment thereof of the present invention and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human PAI-1 antibody or the antigen-binding fragment thereof of the present invention and an expression vector comprising a polynucleotide comprising a base sequence encoding the light chain variable region of the antibody or the antigen-binding fragment thereof; and (c) a host cell transformed with an expression vector comprising a polynucleotide comprising a base sequence encoding the heavy chain variable region of the anti-human PAI-1 antibody or the antigen-binding fragment thereof of the present invention and a host cell transformed with an expression vector comprising a polynucleotide comprising a base sequence encoding the light chain variable region of the antibody or the antigen-binding fragment thereof.

In one embodiment, the method for producing the anti-human PAI-1 antibody of the present invention includes a method for producing an anti-human PAI-1 antibody, comprising culturing host cell(s) selected from the group consisting of the following (a) to (c) to express the anti-human PAI-1 antibody:

(a) a host cell transformed with an expression vector comprising a polynucleotide comprising a base sequence encoding the heavy chain of the anti-human PAI-1 antibody of the present invention and a polynucleotide comprising a base sequence encoding the light chain of the antibody;

(b) a host cell transformed with an expression vector comprising a polynucleotide comprising a base sequence encoding the heavy chain of the anti-human PAI-1 antibody of the present invention and an expression vector comprising a polynucleotide comprising a base sequence encoding the light chain of the antibody; and (c) a host cell transformed with an expression vector comprising a polynucleotide comprising a base sequence encoding the heavy chain of the anti-human PAI-1 antibody of the present invention and a host cell transformed with an expression vector comprising a polynucleotide comprising a base sequence encoding the light chain of the antibody.

The method for producing the anti-human PAI-1 antibody or the antigen-binding fragment thereof of the present invention is not particularly limited as long as it includes a step of culturing the transformed host cells of the present invention to express the anti-human PAI-1 antibody or an antigen-binding fragment thereof. Examples of the preferred host cells used in the method include the preferred transformed host cells of the present invention as described above.

The transformed host cell can be cultured by known methods. Culture conditions, for example, the temperature, pH of culture medium, and the culture time are appropriately selected. In a case where the host cell is an animal cell, examples of the culture medium include MEM culture medium supplemented with approximately 5% to 20% of fetal bovine serum (Science, 1959, Vol. 130, No. 3373, p. 432-7), DMEM culture medium (Virology, 1959, Vol. 8, p. 396), and RPMI1640 culture medium (J. Am. Med. Assoc., 1967, Vol. 199, p. 519), a 199 culture medium (Exp. Biol. Med., 1950, Vol. 73, p. 1-8). The pH of the culture medium is preferably approximately 6 to 8, and the culture is generally carried out at approximately 30° C. to 40° C. for approximately 15 hours to 72 hours while air ventilating and stirring if necessary. In a case where the host cell is an insect cell, as the culture medium, for example, Grace's culture medium (Proc. Natl. Acad. Sci. USA, 1985, Vol. 82, p. 8404) supplemented with fetal bovine serum can be used. The pH of the culture medium is preferably approximately 5 to 8, and the culture is generally carried out at approximately 20° C. to 40° C. for approximately 15 hours to 100 hours while air ventilating and stirring if necessary. In a case where the host cell is *Escherichia coli* or yeast, as the culture medium, for example, liquid culture medium supplemented with a source of nutrients is appropriate. It is preferable that the nutrient culture medium include a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the culture medium is preferably approximately 5 to 8. In a case where the host cell is *Escherichia coli*, preferred examples of the culture medium include LB culture medium and M9 culture medium (Mol. Clo., Cold Spring Harbor Laboratory, 2001, Vol. 3, A2.2). The culture is generally carried out at approximately 14° C. to 39° C. for approximately 3 hours to 24 hours while air ventilating and stirring if necessary. In a case where the host cell is yeast, as the culture medium, for example, Burkholder minimal medium (Proc. Natl. Acad. Sci. USA, 1980, Vol. 77, p. 4505) can be used. The culture is generally carried out at approximately 20° C. to 35° C. for approximately 14 hours to 144 hours while air ventilating and stirring if necessary. By carrying out the culture in the above-described manner, it is possible to express the anti-human PAI-1 antibody or the antigen-binding fragment thereof of the present invention.

The method of producing the anti-human PAI-1 antibody or the antigen-binding fragment thereof of the present invention may include obtaining, preferably isolating or purifying the anti-human PAI-1 antibody or the antigen-binding fragment thereof from the transformed host cell in addition to culturing the transformed host cell of the present invention to express the anti-human PAI-1 antibody or the antigen-binding fragment thereof. Examples of the isolation or purification method include methods using solubility such as salting-out and the solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing phoresis. Preferably, the antibody accumulated in a culture supernatant can be purified by various chromatographies, for example, column chromatography using Protein A column or Protein G column.

The anti-human PAI-1 antibody or the antigen-binding fragment thereof of the present invention also includes an anti-human PAI-1 antibody or an antigen-binding fragment thereof produced by the method for producing the anti-human PAI-1 antibody or the antigen-binding fragment thereof of the present invention.

<Pharmaceutical Composition of the Present Invention>

The pharmaceutical compositions of the present invention include a pharmaceutical composition comprising the anti-human PAI-1 antibody or the antigen-binding fragment thereof of the present invention and pharmaceutically acceptable excipients. The pharmaceutical composition of the present invention can be prepared by a method being generally used with excipients, that is, excipients for medicine, carriers for medicine, and the like being generally used in the field. Examples of dosage forms of the pharmaceutical compositions include parenteral drug such as an injection drug and a drip infusion drug, and these can be administered by intravenous administration, subcutaneous administration, or the like. In drug preparation, excipients, carriers, additives, and the like in accordance with the dosage forms can be used within the pharmaceutically acceptable range.

The pharmaceutical compositions of the present invention may include plural kinds of anti-human PAI-1 antibodies or antigen-binding fragments thereof of the present invention. For example, the present invention includes a pharmaceutical composition comprising an antibody or an antigen-binding fragment thereof, which does not undergo post-translational modification and an antibody or an antigen-binding fragment thereof derived from post-translational modification of the antibody or the antigen-binding fragment thereof.

In one embodiment, the pharmaceutical composition of the present invention, comprising an anti-human PAI-1 antibody or an antigen-binding fragment thereof, includes a pharmaceutical composition described below.

A pharmaceutical composition comprising an anti-human PAI-1 antibody or the antigen-binding fragment thereof, comprising a heavy chain variable region consisting of the amino acid sequence of amino acid numbers 1 to 118 of SEQ ID NO: 2 and a light chain variable region consisting of the amino acid sequence of amino acid numbers 1 to 108 of SEQ ID NO: 4, and an antibody or an antigen-binding fragment thereof which is derived from post-translational modification of the antibody or the antigen-binding fragment thereof.

The pharmaceutical compositions of the present invention include a pharmaceutical composition comprising an antibody in which lysine of the C terminal of the heavy chain is deleted, an antibody or an antigen-binding fragment thereof with post-translational modification to N terminal, an antibody in which lysine of the C terminal of the heavy chain is deleted and post-translation modification to N terminal is made, and/or an antibody which has lysine of the C terminal of the heavy chain and does not have post-translational modification to N terminal.

In one embodiment, the pharmaceutical composition of the present invention, comprising an anti-human PAI-1 antibody, includes a pharmaceutical composition comprising at least two kinds of anti-human PAI-1 antibodies selected from following (1) to (4).

(1) An anti-human PAI-1 antibody comprising a heavy chain consisting of the amino acid sequence of amino acid numbers 1 to 447 of SEQ ID NO: 2 and a light chain consisting of the amino acid sequence shown by SEQ ID NO: 4.

(2) An anti-human PAI-1 antibody comprising a heavy chain consisting of the amino acid sequence of SEQ ID NO: 2 in which glutamic acid of amino acid number 1 is modified to pyroglutamic acid and a light chain consisting of the amino acid sequence shown by SEQ ID NO: 4.

(3) An anti-human PAI-1 antibody comprising a heavy chain consisting of the amino acid sequence of amino acid numbers 1 to 447 of SEQ ID NO: 2 in which glutamic acid of amino acid number 1 is modified to pyroglutamic acid and a light chain consisting of the amino acid sequence shown by SEQ ID NO: 4.

(4) An anti-human PAI-1 antibody comprising a heavy chain consisting of the amino acid sequence shown by SEQ ID NO: 2 and a light chain consisting of the amino acid sequence shown by SEQ ID NO: 4.

In another embodiment, the pharmaceutical composition of the present invention, comprising an anti-human PAI-1 antibody or an antigen-binding fragment thereof, includes a pharmaceutical composition comprising described below.

A pharmaceutical composition comprising an anti-human PAI-1 antibody comprising a heavy chain consisting of the amino acid sequence shown by SEQ ID NO: 2 and a light chain consisting of the amino acid sequence shown by SEQ ID NO: 4; an anti-human PAI-1 antibody comprising a heavy chain consisting of the amino acid sequence of amino acid numbers 1 to 447 of SEQ ID NO: 2 and a light chain consisting of the amino acid sequence shown by SEQ ID NO: 4; and a pharmaceutically acceptable excipient.

The addition amount of the anti-human PAI-1 antibody or the antigen-binding fragment thereof of the present invention in the above formulation varies depending on the degree of a patient's symptoms, the age of a patient, a dosage form of the drug to be used, the binding titer of the antibody, or the like, and for example, an addition amount of approximately 0.001 mg/kg to 100 mg/kg can be used.

The pharmaceutical composition of the present invention may be used as an agent for preventing or treating a disease where active human PAI-1 is involved in the pathogenesis thereof, for example, pulmonary fibrosis such as idiopathic pulmonary fibrosis.

The present invention includes a pharmaceutical composition for preventing or treating pulmonary fibrosis such as idiopathic pulmonary fibrosis, comprising the anti-human PAI-1 antibody or the antigen-binding fragment thereof of the present invention. Further, the present invention includes a method for treating or preventing pulmonary fibrosis such as idiopathic pulmonary fibrosis, comprising a step of administering a therapeutically effective amount of the anti-human PAI-1 antibody or the antigen-binding fragment thereof of the present invention. Further, the present invention includes the anti-human PAI-1 antibody or the antigen-binding fragment thereof of the present invention for use in preventing or treating pulmonary fibrosis such as idiopathic pulmonary fibrosis. Further, the present invention includes use of the anti-human PAI-1 antibody or the antigen-binding fragment thereof of the present invention, in the manufacture of a pharmaceutical composition for preventing or treating pulmonary fibrosis such as idiopathic pulmonary fibrosis.

<Fusion Antibody and Modified Antibody>

Any person skilled in the art can prepare a fusion antibody of an antibody or an antigen-binding fragment thereof with another peptide or protein and can also prepare a modified antibody having a modifying agent bound thereto, using a known method in the art. The anti-human PAI-1 antibody or the antigen-binding fragment thereof of the present invention also includes an antibody and an antigen-binding fragment thereof in the form of such a fusion or a modification. For example, the anti-human PAI-1 antibody or an antigen-binding fragment thereof comprising a heavy chain variable region consisting of the amino acid sequence of amino acid numbers 1 to 118 of SEQ ID NO: 2 and a light chain variable region consisting of the amino acid sequence of amino acid numbers 1 to 108 of SEQ ID NO: 4 also includes an anti-human PAI-1 antibody or an antigen-binding fragment thereof fused with another peptide or protein, and an anti-human PAI-1 antibody or an antigen-binding fragment thereof having a modifying agent bound thereto. The other peptide or protein used for the fusion is not particularly limited, as long as the antibody or the antigen-binding fragment thereof of the present invention as the fusion antibody has a binding activity to a VTN-PAI-1 complex; examples thereof include human serum albumin, various tag peptides, artificial helix motif peptide, maltose-binding proteins, glutathione S transferase, various toxins, other peptides or proteins capable of promoting multimerization, and the like. The modifying agent used for the modification is not particularly limited, as long as the antibody or the antigen-binding fragment thereof of the present invention as the modified antibody has a binding activity to a VTN-PAI-1 complex; examples thereof include polyethylene glycol, sugar chains, phospholipids, liposomes, low-molecular compounds and the like.

The present invention has been described and specific examples referred to for better understanding will be provided, but these are merely examples and the present invention is not limited thereto.

EXAMPLES

With regard to parts using commercially available kits or reagents, the experiments were carried out according to the attached protocol unless otherwise noted. For the sake of convenience, the concentration mol/L is expressed as M. For example, a 1M sodium hydroxide aqueous solution refers to a 1 mol/L aqueous solution of sodium hydroxide.

Example 1

Examination of Immunizing Antigen and Preparation of Anti-Human PAI-1 Antibody-Producing Hybridoma To obtain an antibody having high selectivity for active human PAI-1, an examination was made on an optimal human PAI-1 peptide antigen. As a result of examining the peptide length and amino acid sequence, it was found that it is possible to obtain an antibody which neutralizes active human PAI-1 in the plasma, in the case where a peptide antigen having a Multiple Antigen Peptide 8 (MAP8) peptide (J. Biol. Chem., 1988, Vol. 263, No. 4, p. 1719-1725) connected to the C terminal of a peptide antigen STAVIVSARMAPEEII (SEQ ID NO: 5) of 16 amino acid residues in human PAI-1 are immunized. As a further result of an inventive examination on proteins being connected to an antigen, immune methods and the like, it was found that it is possible to obtain an antibody which potently neutralizes active human PAI-1 in the plasma and has high selectivity for active human PAI-1 in complex with vitronectin (VTN-PAI-1 complex), in the case where a peptide antigen having a Keyhole Limpet Hemocyanin (KLH) protein connected to the C terminal of such a peptide antigen and recombinant active human PAI-1 (Molecular Innovations Inc., PAI-A) are mixed and simultaneously immunized.

Human monoclonal antibody development technology "VelocImmune" (VelocImmune antibody technology: Regeneron, Inc. (U.S. Pat. No. 6,596,541)) mice were used to prepare an antibody. Specifically, a peptide antigen having a KLH protein connected to the C terminal of a peptide antigen STAVIVSARMAPEEII (SEQ ID NO: 5) of 16 amino acid residues in human PAI-1 and recombinant active human PAI-1 (Molecular Innovations Inc., PAI-A) were immunized into VelocImmune mice, together with an adjuvant that elicits an immune reaction. The mice were immunized several times to confirm an increase in antibody titer in the plasma. Finally, immunization was carried out seven times. Thereafter, according to a conventional method, a lymph node of the immunized mice was extracted, and lymphocytes were collected and cell-fused with mouse-derived myeloma cells SP2/0(ATCC: CRL-1581), thereby preparing hybridomas. Limiting dilution samples of hybridomas were prepared to carry out monoclonization. Each clone was subjected to expansion culture. Then, the medium was changed to a CD Hybridoma medium (Invitrogen) which is a serum-free medium, followed by culturing for about one week. The antibody was purified from the resulting culture supernatant using a protein G column (GE Healthcare). Since the VelocImmune technology employs transgenic mice in which the endogenous immunoglobulin heavy and light chain variable regions are replaced with the corresponding human variable regions, the antibody obtained is an antibody having variable regions of the human antibody and constant regions of the mouse antibody (also referred to as a chimeric antibody).

Example 2

ELISA Assay

An ELISA assay was used in order to measure the antigen-specific binding activity of an antibody. In order to evaluate the selectivity for active human PAI-1, tests are carried out using a plate which was prepared by immobilizing vitronectin and adding active human PAI-1, and a plate which was prepared by adding latent human PAI-1 instead of active human PAI-1.

Vitronectin (BD Biosciences, 354238) was diluted to 1000 ng/mL in phosphate-buffered saline (PBS), and added at 100 µL/well to a Nunc MaxiSorp clear 96-well plate (Nunc Inc.) which was then allowed to stand overnight at 4° C. to immobilize the vitronectin. The vitronectin-coating solution was removed by reverse centrifugation, and recombinant active human PAI-1 (Molecular Innovations Inc., PAI-A) or recombinant latent human PAI-1 (Molecular Innovations Inc., PAI-L) diluted to a concentration of 1000 ng/mL in PBS was added at 100 µL/well, followed by allowing to stand at 4° C. for 1 hour. The solution was removed by reverse centrifugation, and a blocking agent (NACALAI TESQUE, INC., 03953-95) solution diluted 3-fold in PBS was added at 200 µL/well. After standing at room temperature for 1 hour, the blocking agent was removed by reverse centrifugation. The purified antibody samples were diluted in seven steps in a range from 1000 ng/mL to 0.1 ng/mL for the plate to which active human PAI-1 had been added, and in a range from 3000 ng/mL to 0.3 ng/mL for the plate to which latent human PAI-1 had been added, using a blocking agent (NACALAI TESQUE, INC., 03953-95) solution diluted 20-fold in PBS, and then added at 100 µL/well. A well to which a blocking agent solution diluted 20-fold in PBS had been added instead of an antibody was prepared as a control. After incubation at room temperature for 1 hour, the plates were washed three times with a washing solution (0.05% Tween-20-containing Tris-buffered saline (TBS)), and 100 µL of an HRP-labeled rabbit anti-mouse Ig antibody (DAKO, P260) which had been diluted 2000-fold with a blocking agent solution diluted 20-fold in PBS was added thereto. After incubation at room temperature for 30 minutes, the plates were washed three times with a washing solution. 100 µL of a color developing solution contained in a peroxidase color development kit (Sumitomo Bakelite Co., Ltd.) was added, followed by allowing to stand at room temperature for about 15 minutes, 100 µL of a reaction stop solution contained in the color development kit was added, and then the OD450 value was measured using an EnVision counter (PerkinElmer Co., Ltd.).

In connection with the calculation of a PAI-1 binding rate at each concentration of each antibody, the measurement value of the well to which a blocking agent (NACALAI TESQUE, INC., 03953-95) solution diluted 20-fold in PBS was added instead of an antibody was taken to be 0%, and the maximum value of the measurement value of each antibody was set to 100%. The PAI-1 binding rate calculated from the measurement value was analyzed to calculate EC50 values of the antibodies by four-parameter logistic curve regression.

As a result, the antibody designated HOT-1 (chimeric antibody) was found to have a higher binding activity selectively for VTN-PAI-1 complex than for latent PAI-1.

Example 3

Production of Fully Human Antibody

The aforementioned antibody is an antibody in which the variable region is human-derived and the constant region is mouse-derived. Accordingly, the present inventors constructed an expression vector comprising both genes of the heavy chain and the light chain using a GS vector (Lonza, Inc.) which is a mammalian cell expression vector, thereby preparing a fully human antibody. Specifically, with respect to HOT-1 identified in Example 2, RNA was extracted from the hybridoma, and cDNA was prepared using a cDNA amplification kit (SMARTer RACE cDNA Amplification kit; Clontech). Then, the variable regions of the heavy and light chains were elongated and amplified using a polymerase chain reaction (PCR). A gene encoding a signal sequence (Nigel Whittle et al., Protein Engineering, 1987, Vol. 1, No. 6, p. 499-505) was connected to the 5' side of the heavy chain variable region gene of HOT-1 and a constant region gene of human Igγ1 (consisting of the base sequence of base numbers 355 to 1344 of SEQ ID NO: 1) was connected to the 3' side thereof, and then this heavy chain gene was inserted into a GS vector pEE6.4. Further, a gene encoding a signal sequence (Nigel Whittle, et al., supra) was connected to the 5' side of the light chain variable region gene of HOT-1 and a constant region gene of the human κ chain (consisting of the base sequence of base numbers 325 to 642 of SEQ ID NO: 3) was connected to the 3' side thereof, and then this light chain gene was inserted into a GS vector pEE12.4.

The heavy chain gene sequence of an antibody inserted into pEE6.4, and the light chain gene sequence of an antibody inserted into pEE12.4 were analyzed using a sequencer, and from the resulting amino acid sequence, the CDR sequences were determined with reference to the database of Kabat et al ("Sequences of Proteins of Immunological Interest", US Department of Health and Human Services, US Government Printing Office).

The base sequence of the heavy chain of the prepared fully human antibody of HOT-1 (fully human HOT-1) is set forth in SEQ ID NO: 1, the amino acid sequence encoded by the base sequence is set forth in SEQ ID NO: 2, the base sequence of the light chain of the antibody is set forth in SEQ ID NO: 3, and the amino acid sequence encoded by the base sequence is set forth in SEQ ID NO: 4. The heavy chain variable region set forth in SEQ ID NO: 2 consists of the amino acid sequence of amino acid numbers 1 to 118 of SEQ ID NO: 2, and the CDR1, CDR2, and CDR3 of the heavy chain each consist of the amino acid sequence of amino acid numbers 31 to 35, 50 to 66, and 99 to 107 of SEQ ID NO: 2. The variable region of the light chain set forth in SEQ ID NO: 4 consists of the amino acid sequence of amino acid numbers 1 to 108 of SEQ ID NO: 4, and the CDR1, CDR2, and CDR3 of the light chain each consist of the amino acid sequence of amino acid numbers 24 to 34, 50 to 56, and 89 to 97 of SEQ ID NO: 4.

The above-described GS vector into which the genes of the heavy chain and the light chain of fully human HOT-1 were respectively inserted was cleaved by restriction enzymes NotI and PvuI, and subjected to ligation using a DNA Ligation Kit (Takara Bio Inc.), thereby constructing a GS vector into which both genes of the heavy chain and the light chain were inserted. The antibody expression was carried out in two ways of transient expression and constitutive expression using this GS vector. For the transient expression, the GS vector was transfected into FreeStyle 293 cells (Invitrogen) cultured at about $1 \times 10^6$ cells/mL in a FreeStyle 293 Expression medium (Invitrogen) using a transfection reagent FreestyleMAX (Invitrogen), and cultured for 7 days. The purified antibody of the fully human antibody was obtained from the culture supernatant using a Protein G column (GE Healthcare). For the constitutive expression, the GS vector was transfected into CHO-K1 SV cells (Lonza, Inc.) using an electroporation method, thereby resulting in antibody expression. The fully human antibody was purified from the culture supernatant using a Protein A column (GE Healthcare).

Example 4

Analysis of Amino Acid Modifications of Fully Human Antibody

As a result of analyzing the amino acid modifications of the purified fully human HOT-1, the deletion of lysine at the C terminal of the heavy chain has occurred in most of the purified antibodies.

Example 5

Measurement of Inhibitory Activity on Active PAI-1 in Human Plasma

To evaluate an inhibitory activity on active PAI-1 in human plasma for HOT-1 identified in Example 2 (chimeric antibody) and fully human HOT-1 prepared in Example 3, an active PAI-1 inhibition assay was carried out using the plasma of obese patients. In the case of using normal human plasma, since the concentration of active PAI-1 is low and it is difficult to construct an assay system, the plasma of obese patients, for which it is known that the concentration of active PAI-1 in the plasma is high, was used (Nature Medicine, 1996, Vol. 2, p. 800-803).

uPA (intravenous urokinase $6 \times 10^4$ units "Benesis (registered trademark)"; Mitsubishi Tanabe Pharma Corporation) was diluted to 50 units/mL in PBS, and added at 100 μL/well to an assay plate Nunc MaxiSorp white 96-well plate (Nunc Inc.) which was then allowed to stand overnight at 4° C. to immobilize the uPA. The coating solution was removed by reverse centrifugation, and a blocking agent (NACALAI TESQUE, INC., 03953-95) solution diluted 3-fold in PBS was added at 200 μL/well, followed by allowing to stand at room temperature for 1 hour.

Meanwhile, a mixture of obese patient plasma and antibody sample (plasma-antibody mixture) was prepared. Specifically, the plasma was diluted using PBS containing 0.1% bovine serum-derived albumin (BSA), such that the obese patient plasma was diluted 35-fold when the plasma-antibody mixture was prepared (the concentration of human plasma-derived active PAI-1 contained in the plasma-antibody mixture is about 360 pg/mL). Further, the antibody sample was diluted in seven-step dilution series using a 0.1% BSA-containing PBS, such that the final concentration of an antibody was in a range from 1000 ng/mL to 1 ng/mL. Then, the plasma and the antibody sample were mixed to prepare a plasma-antibody mixture. As a calibration curve sample, recombinant active human PAI-1 (Molecular Innovations Inc., PAI-A) was prepared which had been diluted in 7 steps in a range from 10000 pg/mL to 10 pg/mL in 0.1% BSA-containing PBS. As a control sample, a sample in which the obese patient plasma had been mixed with 0.1% BSA-containing PBS instead of an antibody was prepared. These plasma-antibody mixtures, calibration curve sample, and control sample were allowed to stand at room temperature for 30 minutes and pre-incubated.

After the blocking agent in the assay plate was removed by reverse centrifugation, the pre-incubated plasma-antibody mixtures, the calibration curve sample, and the control sample were added at 100 μL/well to the assay plate which was then allowed to stand at room temperature for 30 minutes. The plate was washed three times with a washing solution (0.05% Tween-20-containing TBS), and anti-PAI-1 antibodies (Progen Biotechnik, MA-33H1F7) diluted 3,000-fold with a blocking agent (NACALAI TESQUE, INC., 03953-95) solution which had been diluted 20-fold in PBS were added thereto at 100 μL/well. After allowing to stand at room temperature for 30 minutes, the plate was washed three times with a washing solution, and biotinylated anti-mouse Ig antibodies (Ancell, 234010) diluted 2,000-fold with a blocking agent (NACALAI TESQUE, INC., 03953-95) solution which had been diluted 20-fold in PBS were added thereto at 100 μL/well. After allowing to stand at room temperature for 30 minutes, the plate was washed three times with a washing solution, and alkaline phosphatase-labeled streptavidin (Thermo Scientific) diluted 1,000-fold with a blocking agent (NACALAI TESQUE, INC., 03953-95) solution which had been diluted 20-fold in PBS was added thereto at 100 μL/well. After incubation at room temperature for 30 minutes, the plate was washed three times with a washing solution. An alkaline phosphatase substrate (Chemiluminescent AP; SurModics, APU4-0100-01) 5-fold diluted in a 0.1 mM magnesium chloride aqueous solution containing 2 mM Tris (pH 9.8) was added at 100 μL/well, and the signal value was measured using an EnVision counter (PerkinElmer Co., Ltd.).

The concentration of active human PAI-1 was calculated using a calibration curve. The test was carried out in duplicate for each antibody, and the average value was calculated. The concentration of active human PAI-1 in the well to which a sample where 0.1% BSA-containing PBS instead of an antibody had been mixed with the plasma of obese patients was added was set to 100%, and the concentration of active human PAI-1 in the well where 1000 ng/mL of the antibody had been mixed with the plasma of obese patients was set to 0%. The calculated active human PAI-1 inhibitory rate was analyzed to calculate IC50 values of the antibodies by four-parameter logistic curve regression.

As a result, it was demonstrated that the IC50 value of HOT-1 (chimeric antibody) is 11.3 ng/mL and IC50 of fully human HOT-1 is 6.0 ng/mL, and both of antibodies inhibit the uPA-binding activity of active PAI-1 in human plasma.

Example 6

Evaluation of Binding Selectivity for VTN-PAI-1 Complex

An ELISA assay was used to evaluate the binding selectivity of fully human HOT-1 prepared in Example 3 for VTN-PAI-1 complex. Four human PAI-1-immobilized plates of the following (1) to (4) were prepared, and the tests were carried out using each plate.

(1) VTN-PAI-1 Complex-Immobilized Plate

Vitronectin (BD Biosciences, 354238) was diluted to 1000 ng/mL in PBS, and added at 100 μL/well to a Nunc MaxiSorp clear 96-well plate (Nunc Inc.) which was then allowed to stand overnight at 4° C. to immobilize the vitronectin. The coating solution was removed by reverse centrifugation, and a blocking agent (Thermo Scientific, 37532) was added at 200 μL/well, followed by allowing to stand at room temperature for 30 minutes. Recombinant active human PAI-1 (Molecular Innovations Inc., PAI-A) diluted to 1000 ng/mL in 0.1% BSA-containing PBS was added at 100 μL/well and allowed to be captured on the vitronectin. The binding activity of the antibody for VTN-PAI-1 was evaluated by the test in this plate.

(2) Latent Human PAI-1-Immobilized Plate

Recombinant latent human PAT-1 (Molecular Innovations Inc., PAI-L) was diluted to 1000 ng/mL in PBS, and added at 100 μL/well to a Nunc MaxiSorp clear 96-well plate (Nunc Inc.) which was then allowed to stand overnight at 4° C. to immobilize the latent human PAI-1. The coating solution was removed by reverse centrifugation, and a blocking agent (Thermo Scientific, 37532) was added at 200 μL/well, followed by allowing to stand at room temperature for 30 minutes. The binding activity of the antibody for latent human PAL-1 was evaluated by the test in this plate.

(3) uPA-PAI-1 Complex-Immobilized Plate uPA (intravenous urokinase $6 \times 10^4$ units "Benesis (registered trademark)"; Mitsubishi Tanabe Pharma Corporation) was diluted to 100 units/mL in PBS, and added at 100 μL/well to a Nunc MaxiSorp clear 96-well plate (Nunc Inc.) which was then allowed to stand overnight at 4° C. to immobilize the uPA. The coating solution was removed by reverse centrifugation, and a blocking agent (Thermo Scientific, 37532) was added at 200 μL/well, followed by allowing to stand at room temperature for 30 minutes. Recombinant active human PAL-1 (Molecular Innovations Inc., PAT-A) diluted to 1000 ng/mL in 0.1% BSA-containing PBS was added at 100 μL/well and allowed to be captured on the uPA. The binding activity of the antibody for the uPA-PAI-1 complex was evaluated by the test in this plate.

(4) tPA-PAI-1 Complex-Immobilized Plate tPA (Activacin (registered trademark) for Injection 6,000,000; Kyowa Hakko Kirin Co., Ltd.) was diluted to 1000 units/mL in PBS, and added at 100 μL/well to a Nunc MaxiSorp clear 96-well plate (Nunc Inc.) which was then allowed to stand overnight at 4° C. to immobilize the tPA. The coating solution was removed by reverse centrifugation, and a blocking agent (Thermo Scientific, 37532) was added at 200 μL/well, followed by allowing to stand at room temperature for 30 minutes. Recombinant active human PAI-1 (Molecular Innovations Inc., PAI-A) diluted to 1000 ng/mL in 0.1% BSA-containing PBS was added at 100 μL/well and allowed to be captured on the tPA. The binding activity of the antibody for the tPA-PAI-1 complex was evaluated by the test in this plate.

Each of the prepared human PAI-1-immobilized plates was washed with a washing solution (0.05% Tween-20-containing TBS), and fully human HOT-1, which had been diluted in eight steps in a range from 100,000 ng/mL to 0.01 ng/mL with 0.1% BSA-containing PBS, was added at 100 μL/well, followed by allowing to stand at room temperature for 30 minutes. As comparative antibodies, MEDI-579 (Patent Document 3) which is a fully human anti-human PAI-1 antibody, and MA-33B8 (Progen Biotechnik Ltd.), MA-33H1F7 (Progen Biotechnik, Inc.), MA-55F4C12 (Hycult Biotech Inc., HM2180) and MA-56A7C10 (Hycult Biotech Inc., HM2182) which are mouse anti-human PAI-1 antibodies were diluted in seven steps in a range from 10,000 ng/mL to 0.01 ng/mL using 0.1% BSA-containing PBS, and then added at 100 μL/well, followed by allowing to stand at room temperature for 30 minutes. As a control, a well to which 0.1% BSA-containing PBS had been added instead of an antibody was prepared. After washing three times with a washing solution, a detection antibody diluted 2,000-fold using a blocking agent (NACALAI TESQUE, INC., 03953-95) solution which had been diluted 20-fold in PBS was added at 100 μL/well, followed by the reaction. An HRP-labeled goat anti-mouse Ig antibody (Southern Biotech, 1010-05) for the detection of a test antibody having an Fe region of a mouse antibody and an HRP-labeled rabbit anti-human Ig antibody (Southern Biotech, 6145-05) for the detection of a test antibody having an Fc region of a human antibody are used as the detection antibody. After incubation at room temperature for 30 minutes, the plates were washed three times with a washing solution. A color developing solution contained in a peroxidase color development kit (Sumitomo Bakelite Co., Ltd.) was added at 100 μL/well, followed by allowing to stand at room temperature for about 15 minutes, 100 μL of a reaction stop solution contained in the color development kit was added, and then the OD450 value was measured using an EnVision counter (PerkinElmer Co., Ltd.).

For each plate, the test of each antibody was carried out in duplicate, and the average value was calculated. In connection with the calculation of a PAI-1 binding rate at each concentration of each antibody, the measurement value of a well to which 0.1% BSA-containing PBS had been added instead of an antibody was taken to be 0%, and the measurement value of the maximum concentration in each antibody was set to 100%. Meanwhile, with regard to fully human HOT-1, in the binding activity evaluation system for latent human PAI-1, the uPA-PAI-1 complex and the tPA-PAI-1 complex, the measurement value of the maximum concentration of MEDI-579 in each evaluation system was set to 100% since fully human HOT-1 was added at the maximum concentration but the measurement value did not reach the measurement value of the maximum concentration of MEDI-579 having the same human Fc region. With regard to MA33-B8, in the binding activity evaluation system for the VTN-PAI-1 complex, the measurement value of the maximum concentration in the evaluation system of MA56-A7C10 was set to 100% since it did not reach the measurement value of the maximum concentration of MA56-A7C10 having the same mouse Fc region even when the maximum concentration was added. The calculated PAI-1 binding rate was analyzed to calculate EC50 values of the antibodies by four-parameter logistic curve regression.

Table 1: Binding Activity of Anti-Human PAI-1 Antibody for a Variety of Human PAI-1

TABLE 1

|  | EC50 value (ng/mL) | | | |
| --- | --- | --- | --- | --- |
|  | VTN-PAI-1 | Latent human PAI-1 | Human uPA-PAI-1 | Human tPA-PAI-1 |
| Fully human HOT-1 | 4.2 | 88801 | >100000 | >100000 |
| MEDI-579 | 5.2 | 22.1 | 6.1 | 3.2 |
| MA33-H1F7 | 14.3 | 13.6 | 12.7 | 11.7 |
| MA33-B8 | 5685 | 639.8 | 12.9 | 22.8 |
| MA55-F4C12 | 7.5 | 12.8 | 9.8 | 9.2 |
| MA56-A7C10 | 23.9 | 29.9 | 16.0 | 12.7 |

>100,000 means that the antibody concentration exhibiting 50% of the measurement value of the maximum concentration of MEDI-579 in each evaluation system is greater than 100,000 ng/mL.

As a result, it was demonstrated that fully human HOT-1 exhibits a strong binding activity for the VTN-PAI-1 complex, and also has a very high selective binding activity.

Since fully human HOT-1 has a very high selective binding activity for the VTN-PAI-1 complex as compared with each comparative antibody, it has been suggested that fully human HOT-1 has a binding site to PAI-1 different from that of conventionally known anti-human PAI-1 antibodies, and therefore binds to the active center of human PAI-1 or a site closer thereabout.

Example 7

Evaluation of Binding to Monomeric Active Human PAI-1

In order to measure the binding activity of fully human HOT-1 to monomeric active human PAI-1, SPR analysis was carried out. In SPR analysis, the analysis was carried out using Biacore (registered trademark) T200 (GE Healthcare Japan) and recombinant active human PAI-1 (Molecular Innovations Inc., PAI-A). As a result, it was demonstrated that fully human HOT-1 binds to active human PAI-1 which is present as a monomer.

Example 8

Evaluation of Binding Selectivity for Monkey PAI-1

An ELISA assay was used to evaluate the binding selectivity of fully human HOT-1 for active monkey PAI-1 in complex with vitronectin (also referred to as a VTN-monkey PAI-1 complex). Four monkey PAI-1-immobilized plates of the following (1) to (4) were prepared, and the tests were carried out using each plate. MEDI-579 was used as a comparative antibody.

(1) VTN-Monkey PAI-1 Complex-Immobilized Plate

The binding activity of the antibody for VTN-monkey PAI-1 was evaluated according to the method described in Example 6 (1). Meanwhile, recombinant active monkey PAI-1 (Molecular Innovations Inc., CYPAI) was used instead of recombinant active human PAI-1. Further, fully human HOT-1 and MEDI-579 were diluted in seven steps in a range from 10000 ng/mL to 0.01 ng/mL and then used.

(2) Latent Monkey PAI-1-Immobilized Plate

The binding activity of the antibody for latent monkey PAI-1 was evaluated according to the method described in Example 6 (2). Meanwhile, recombinant latent monkey PAI-1 (Molecular Innovations Inc., CYPAI-L) was used instead of recombinant latent human PAI-1. Further, fully human HOT-1 and MEDI-579 were diluted in seven steps in a range from 10000 ng/mL to 0.01 ng/mL and then used.

(3) uPA-Monkey PAI-1 Complex-Immobilized Plate

The binding activity of the antibody for the uPA-monkey PAI-1 complex was evaluated according to the method described in Example 6 (3). Meanwhile, recombinant active monkey PAI-1 (Molecular Innovations Inc., CYPAI) was used instead of recombinant active human PAI-1. Further, fully human HOT-1 and MEDI-579 were diluted in seven steps in a range from 10000 ng/mL to 0.01 ng/mL and then used.

(4) tPA-Monkey PAI-1 Complex-Immobilized Plate

The binding activity of the antibody for the tPA-monkey PAI-1 complex was evaluated according to the method described in Example 6 (4). Meanwhile, recombinant active monkey PAI-1 (Molecular Innovations Inc., CYPAI) was used instead of recombinant active human PAI-1. Further, fully human HOT-1 and MEDI-579 were diluted in seven steps in a range from 10000 ng/mL to 0.01 ng/mL and then used.

Using each of the prepared monkey PAI-1-immobilized plates, an EC50 value of each antibody was calculated according to the method described in Example 6. Meanwhile, with regard to fully human HOT-1, in the binding activity evaluation system for latent monkey PAI-1, the uPA-monkey PAI-1 complex and the tPA-monkey PAI-1 complex, the measurement value of the maximum concentration of MEDI-579 in each evaluation system was set to 100% since fully human HOT-1 was added at the maximum concentration but the measurement value did not reach the measurement value of the maximum concentration of MEDI-579 having the same human Fc region.

TABLE 2

| Binding activity of anti-PAI-1 antibody for a variety of monkey PAI-1 | | | | |
| --- | --- | --- | --- | --- |
|  | EC50 value (ng/mL) | | | |
|  | VTN-monkey PAI-1 | Latent monkey PAI-1 | uPA-monkey PAI-1 | tPA-monkey PAI-1 |
| Fully human HOT-1 | 3.6 | >10000 | >10000 | >10000 |
| MEDI-579 | 4.1 | 48.2 | 5.4 | 4.3 |

>10,000 means that the antibody concentration exhibiting 50% of the measurement value of the maximum concentration of MEDI-579 in each evaluation system is greater than 10,000 ng/mL.

As a result, it was demonstrated that the fully human HOT-1 antibody exhibits a strong binding activity for the VTN-monkey PAI-1 complex, and also has a very high selective binding activity.

Example 9

Measurement of Inhibitory Activity on Active PAI-1 in Human and Monkey Plasma

The evaluation of an inhibitory activity of fully human HOT-1 and MEDI-579 on active PAI-1 in human and monkey plasma was carried out. With regard to the human plasma, the plasma of obese patients was used in the same manner as in Example 5. With regard to the monkey plasma, plasma collected from cynomolgus monkeys with the intravenous administration of LPS was used.

The evaluation of an inhibitory activity on active PAI-1 in human plasma was carried out according to the method of Example 5. The evaluation of an inhibitory activity on active PAI-1 in monkey plasma was carried out using monkey plasma instead of human plasma in the method described in Example 5. With regard to the monkey plasma, the plasma was diluted using 0.1% BSA-containing PBS, such that the monkey plasma was diluted 120-fold when a plasma-antibody mixture was prepared. For both of two evaluation systems, the final concentration of each antibody was used in a range from 300 ng/mL to 0.3 ng/mL (7-step dilution). As a calibration curve sample, recombinant active human PAI-1 (Molecular Innovations Inc., PAI-A) was used which had been diluted in 7 steps in a range from 3000 pg/mL to 3 pg/mL with 0.1% BSA-containing PBS.

The concentration of each active PAI-1 was calculated using a calibration curve. The test was carried out in duplicate for each antibody, and the average value was calculated. The concentration of active PAI-1 in the well to which a sample where 0.1% BSA-containing PBS instead of an antibody had been mixed with the obese patient plasma or monkey plasma was added was set to 100%, and the concentration of each active PAI-1 in the well where 300 ng/mL of a MEDI-579 antibody had been mixed with the obese patient plasma or monkey plasma was set to 0%. Each of the calculated active PAI-1 inhibitory rates was analyzed to calculate IC50 values of the antibodies by four-parameter logistic curve regression.

As a result, the IC50 value of fully human HOT-1 was 4.2 ng/mL and the IC50 value of MEDI-579 was 0.73 ng/mL, for the uPA-binding activity of active PAI-1 in human plasma. With regard to the uPA-binding activity of active PAI-1 in monkey plasma, the IC50 value of fully human HOT-1 was 37 ng/mL and the IC50 value of MEDI-579 was 0.83 ng/mL.

It was demonstrated that fully human HOT-1 and MEDI-579 inhibit the uPA-binding activity of active PAI-1 in human and monkey plasma.

Example 10

Measurement of PAI-1 Inhibitory Activity in In Vitro Intravascular Reproducing System It is known that uPA and tPA in the blood vessel walls are produced from vascular endothelium and are bound to the vascular endothelium (Bailliers Clin. Haematol., 1993, Vol. 6, No. 3, p. 559-576. Blood, 2011, Vol. 118, No. 11, p. 3182-3185). In other words, uPA and tPA are present in the blood vessel walls as well as in the blood. In Example 9, the inhibitory activity of an anti-PAI-1 antibody on active PAI-1 in the plasma was measured, but this experimental system did not take into consideration the influence of blood vessel walls in the fact that only the components in the plasma are extracted. Therefore, it is hard to consider that such an experimental system is said to reflect actual biological reactions in the blood vessels. For this reason, using an evaluation system where active PAI-1, uPA and uPA substrate peptides were mixed into an assay plate on which a uPA-PAI-1 complex had been immobilized as a system that imitates the actual intravascular state, activities of fully human HOT-1 and MEDI-579 were measured by taking the activity of uPA as an indicator.

Recombinant active human PAI-1 (Molecular Innovations Inc., PAI-A) was diluted to 10 µg/mL in PBS, and added at 100 µL/well to a Nunc MaxiSorp white 96-well plate (Nunc Inc.) which was then allowed to stand at room temperature for 20 minutes to immobilize the active PAI-1. The coating solution was removed by reverse centrifugation, and a blocking agent (NACALAI TESQUE, INC., 03953-95) solution was added at 200 µL/well, followed by allowing to stand at room temperature for 15 minutes. After removing the solution by reverse centrifugation, uPA (intravenous urokinase $6 \times 10^4$ units "Benesis (registered trademark)"; Mitsubishi Tanabe Pharma Corporation) was diluted to 50 units/mL with a blocking agent that had been diluted 3-fold in PBS, and then added at 100 µL/well. After allowing to stand at room temperature for 20 minutes, bicarbonate buffer (Sigma-Aldrich Co., LLC., C3041-50CAP) was added at 200 µL/well, followed by allowing to stand overnight at 37° C.

Using a 0.1% BSA-containing PBS, each antibody was diluted in 10-step dilution series to the final concentration in a range from 500 ng/mL to 0.015 ng/mL. Each antibody solution was mixed recombinant human active PAI-1 diluted to a final concentration of 0.0025 µg/mL in PBS, vitronectin diluted to a final concentration of 0.0025 µg/mL in PBS, Glutarylglycyl-L-arginine 4-methylcoumaryl-7-amide (Peptide Institute, 3097-v), which is a substrate peptide of uPA, diluted to a final concentration of 65 ng/mL in PBS, BSA diluted to a final concentration of 1.25 mg/mL in PBS, and uPA diluted to a final concentration 0.05 units/mL in PBS. As a control, a well to which 0.1% BSA-containing PBS had been added instead of an antibody, and a well in which 0.1% BSA-containing PBS and PBS had been mixed instead of an antibody and recombinant human active PAI-1 were prepared.

After the plate was washed three times with a washing solution (0.05% Tween-20-containing TBS), the above mixture was added at 50 µL/well and allowed to stand at room temperature for 24 hours to result in the progression of an enzymatic reaction where uPA cleaves a substrate peptide. When the substrate peptide is cleaved, a fluorescent substance 7-amino-4-methyl-coumarin is detached from the peptide itself. A sample of each well was collected at 20 µL/well and transferred to a Nunc black 384-well plate (Nunc, Inc.), and fluorescent signal values at an excitation wavelength of 400 nm and a fluorescence wavelength of 505 nm were measured using an EnVision counter (PerkinElmer Co., Ltd.).

The test of each antibody was carried out in duplicate, and the average value was calculated. In connection with the calculation of uPA activity rate at each measurement values of each antibody, the average value of the measurement values of the well to which 0.1% BSA-containing PBS had been added instead of an antibody was taken to be 0%, and the average value of the measurement values of the well to which 0.1%

BSA-containing PBS and PBS had been added instead of an antibody and recombinant human active PAI-1 was set to 100%. The calculated uPA activity rate was analyzed to calculate EC50 values of the antibodies by four-parameter logistic curve regression. Since PAI-1 inhibits an activity of uPA, the uPA activity becomes higher as the human PAI-1 inhibitory activity of the antibody becomes higher.

As a result, an EC50 value of fully human HOT-1 was 12.7 ng/mL and an EC50 value of MEDI-579 was 42.1 ng/mL, taking the activity of uPA in this evaluation system as an indicator. It was demonstrated that fully human HOT-1 has a higher uPA activation ability. Accordingly, in this evaluation system, it was demonstrated that fully human HOT-1 has a higher PAI-1 inhibitory activity.

Example 11

Measurement of Antibody Concentration in Monkey Plasma

From the results of Example 6, it was demonstrated that fully human HOT-1 exhibits a strong binding activity for the VTN-PAI-1 complex, and also has a very high selective binding activity. Generally, it is known that an antibody in the blood binds to an antigen and is then metabolized as an antigen-antibody complex, in addition to that the antibody may be directly metabolized (Journal of Pharmaceutical Sciences, 2012, Vol. 101, No. 12, p 4367-4382). Since PAI-1 in the plasma is present in the form of latent PAI-1 and various complexes such as tPA-PAI-1 complexes in addition to VTN-PAI-1 (Blood, 1990, Vol. 76, p. 930-937), an anti-PAI-1 antibody having low selectivity forms an antigen-antibody complex with various PAI-1 and is then metabolized. On the other hand, fully human HOT-1 selectively binds to VTN-PAI-1 and thus is hardly metabolized as a complex with latent PAI-1 or PA-PAI-1, and correspondingly there was considered possibility of long-term duration of the fully human HOT-1 concentration in the blood. In fact, it is known that the blood concentration duration of antibodies is highly dependent on the metabolic rate of this antigen-antibody complex (Bioanalysis, 2011, Vol. 3, No. 6, p. 659-675). From the results of Example 8, since fully human HOT-1 exhibited a high selective binding activity for the VTN-monkey PAI-1 complex, the antibody concentration in the plasma upon administration of the antibody to monkeys was determined. MEDI-579 was used as a comparative antibody.

A fully human HOT-1 or MEDI-579 diluted in PBS was intravenously administered to cynomolgus monkeys. The treated groups were set as follows.

[Treated Groups]
HOT-1-administered group (n=3):
A group to which fully human HOT-1 was administered (2.0 mg/kg)
MEDI-579-administered group (n=2):
A group to which MEDI-579 was administered (2.0 mg/kg)

Blood was collected before antibody administration, and at 0.25, 1, 2, 4, 8, 24, 48, 96, 168, 336 and 504 hours after antibody administration to obtain the plasma. With respect to fully human HOT-1, blood was further collected after 672, 936, 1200 and 1440 hours to obtain the plasma.

The concentration of each antibody in the plasma was measured by an electrochemiluminescence (ECL) assay.

The ECL assay of fully human HOT-1 is shown below. Vitronectin was diluted to 100 ng/mL in TBS, and was added at 25 µL/well using a Multi-array 96-well Plate (Meso Scale Discovery, L15XA-1). The plate was allowed to stand overnight at 4° C. to immobilize vitronectin on the plate. The vitronectin-coating solution was removed by reverse centrifugation, and the plate was washed three times with a washing liquid (0.05% Tween-20-containing TBS). Recombinant active human PAI-1 (Molecular Innovations Inc., PAI-A) diluted to 100 ng/mL in TBS was added at 25 µL/well, followed by allowing to stand at 4° C. for 1 hour to result in immobilization. The coating solution was removed by reverse centrifugation, the plate was washed three times with a washing solution, and a blocking agent 1 (Thermo Scientific, 37532) was added at 150 µL/well. After allowing to stand at room temperature for 1 hour, the blocking agent 1 was removed by reverse centrifugation and the plate was washed three times with a washing solution. The plasma of monkeys to which an antibody had been administered was diluted 100-fold in a 0.05% Tween-20-containing blocking agent 1 solution, further diluted to be within the range of a calibration curve, using a 0.05% Tween-20-containing blocking agent 1 solution containing 1% plasma of monkeys to which an antibody had not been administered (hereinafter, referred to as a plasma-Tween-containing blocking agent 1 solution), and then added at 25 µL/well. For the preparation of a calibration curve, a well to which the fully human HOT-1 diluted in 11 steps in a range from 100 ng/mL to 0.0017 ng/mL using the plasma-Tween-containing blocking agent 1 solution had been added was prepared. As a control, a well to which the plasma-Tween containing blocking agent 1 solution had been added instead of an antibody was prepared. After incubation at room temperature for 1 hour, the solution was removed by reverse centrifugation, followed by washing three times with a washing solution. 25 µL of monkey immunoglobulin-absorbed anti-human IgG light chain biotin (Immuno-Biological Laboratories, 17249) diluted to 80 ng/mL using a 0.05% Tween-20-containing blocking agent 1 solution was added thereto. After incubation at room temperature for 1 hour, the solution was removed by reverse centrifugation, followed by washing three times with a washing solution. 25 µL of MSD SULFO-TAG Streptavidin (Meso Scale Discovery, R32AD-1) diluted to 20 ng/mL using a 0.05% Tween-20-containing blocking agent 1 solution was added thereto. After incubation at room temperature for 1 hour, the solution was removed by reverse centrifugation, followed by washing three times with a washing solution. 150 µL of MSD Read Buffer T(4x) with Surfactant (Meso Scale Discovery, R92TC-2) diluted 2-fold in ultrapure water (MilliQ (registered trademark), Merck KGaA) was added, and the electrochemiluminescence was measured using a SECTOR Imager 6000 (Meso Scale Discovery).

The concentration of MEDI-579 in the plasma was measured according to the ECL assay method of fully human HOT-1. Meanwhile, vitronectin and recombinant active human PAI-1 were used at a concentration of 75 ng/mL. As a blocking step after the immobilization of recombinant active PAI-1, the following blocking treatment was carried out instead of treatment with the blocking agent 1. A blocking agent 2 (Meso Scale Discovery, R93BA-1) dissolved to 5 w/v % in TBS was added at 150 µL/well and the plate was allowed to stand at room temperature for 1 hour. The blocking agent was removed, the plate was washed three times with a washing solution, and then a blocking agent 3 (Meso Scale Discovery, R51BB-3) which had been diluted 4-fold in the blocking agent 1 was added at 50 µL/well.

In calculating the antibody concentration, a calibration curve was prepared. The analysis of the regression equation was carried out in a five-parameter logistic model. Weighting was $1/y^2$. The antibody concentration at each blood collection point was calculated from the calibration curve. The test of each plasma was carried out in triplicate to obtain an average value of the calculated concentrations. The resulting antibody concentrations were analyzed for each test material and each test monkey by using a BioBook (IDBS, Inc.). The half-life of the antibody was calculated from the slope of the β phase of a graph depicting the vertical axis as a logarithmic value of the antibody concentration and the horizontal axis as a blood collection time.

As a result, the half-life of MEDI-579 was 52.6 hours whereas the half-life of fully human HOT-1 was 255 hours. It was demonstrated that fully human HOT-1 has a longer duration in the blood.

Example 12

Measurement of Inhibitory Activity on Active PAI-1 in Monkey Blood

The long-lasting and strong inhibition of the PAI-1 activity in the blood of monkeys is desirable for the prevention or treatment of a disease in which PAI-1 is involved in the pathogenesis thereof, such as pulmonary fibrosis. Accordingly, the inhibitory activity of fully human HOT-1 on active PAI-1 in monkey blood was evaluated. MEDI-579 was used as a comparative antibody.

The inhibitory activity on active PA-1 in the blood was measured using the plasma obtained from monkeys dosed with fully human HOT-1 or MEDI-579 in Example 11.

uPA (intravenous urokinase $6\times10^4$ units "Benesis (registered trademark)"; Mitsubishi Tanabe Pharma Corporation) was diluted to 50 units/mL in PBS, and added at 100 μL/well to a Nunc MaxiSorp white 96-well plate (Nunc Inc.) which was then allowed to stand overnight at 4° C. to immobilize the uPA. The coating solution was removed by reverse centrifugation, and a blocking agent (Thermo Scientific, 37532) was added at 200 μL/well, followed by allowing to stand at room temperature for 1 hour. The plate was washed with a washing solution (0.05% Tween-20-containing TBS), and the plasma diluted 10-fold in 0.1% BSA-containing PBS was added at 100 μL/well, followed by allowing to stand at room temperature for 30 minutes. For a calibration curve, human active PAI-1 (Molecular Innovations Inc., PAI-A) was diluted in seven steps in a range from 300 ng/mL to 0.003 ng/mL using 0.1% BSA-containing PBS, added at 100 μL/well, and allowed to stand simultaneously with the plasma at room temperature for 30 minutes. As a control, a well to which 0.1% BSA-containing PBS had been added instead of an antibody was prepared. The plate was washed three times with a washing solution, and the biotinylated (Dojindo Molecular Technologies, Inc., LK03) anti-PAI-1 antibody (Progen Biotechnik, MA-33H1F7) diluted 10,000-fold using a blocking agent (NACALAI TESQUE, INC., 03953-95) solution which had been diluted 20-fold in PBS was added at 100 μL/well, followed by the reaction. Here, from the results of Example 6, MA-33H1F7 was used as an anti-PAI-1 antibody which recognizes the uPA-PAI-1 complex on the plate. The biotinylation was carried out according to the method instructed in the kit of Dojindo Molecular Technologies, Inc. After incubation at room temperature for 1 hour, the plate was washed three times with a washing solution, and streptavidin-AL (Thermo Scientific, 21324) diluted 1000-fold using a blocking agent (NACALAI TESQUE, INC., 03953-95) solution which had been diluted 20-fold in PBS was added at 100 μL/well. After incubation at room temperature for 1 hour, the plate was washed three times with a washing solution, and an alkaline phosphatase substrate (Chemiluminescent AP; SurModics, APU4-0100-01) 5-fold diluted in a 2 mM Tris (pH 9.8)-containing 0.1 mM magnesium chloride aqueous solution was added at 100 μL/well. After allowing to stand at room temperature for 30 minutes, the signal value was measured using an EnVision counter (PerkinElmer Co., Ltd.).

The concentration of active PAI-1 was calculated using a calibration curve. The results of an inhibitory effect of each antibody on active PAI-1 in monkey plasma are shown in FIG. 1. The test was carried out in duplicate for each plasma and the average value was calculated. In addition, values of monkey plasma of each group used in the test were averaged. The active PAI-1 concentration before antibody administration was taken to be 100%, and the active PAI-1 concentration of 0 ng/mL for the calibration curve was taken to be 0% to calculate an inhibitory rate from the active PAI-1 concentration in each plasma, and the number of days that can inhibit 50% or more of the active PAI-1 concentration in the plasma after antibody administration relative to before antibody administration was calculated.

As a result, the number of days that can inhibit 50% or more of the active PAI-1 concentration in the plasma was 28 days in the group to which fully human HOT-1 was administered, and 7 days in the group to which MEDI-579 was administered. It was demonstrated that fully human HOT-1 exhibits longer-lasting and stronger inhibition of active PAI-1 in the plasma, when compared with MEDI-579.

INDUSTRIAL APPLICABILITY

The anti-human PAI-1 antibodies of the present invention are useful for the prevention or treatment of various diseases where active human PAI-1 is involved in the pathogenesis thereof. Further, polynucleotides, expression vectors, transformed host cells and methods for producing antibodies of the present invention are useful for the production of the above-mentioned anti-human PAI-1 antibodies.

[Sequence List Free Text]

In the number heading <223> of the sequence list, description of "Artificial Sequence" is made. Specifically, the base sequences shown by SEQ ID NOS: 1 and 3 of the sequence list are the base sequences of the heavy chain and the light chain of the fully human HOT-1, respectively, and the amino acid sequences shown by SEQ ID NOS: 2 and 4 are the amino acid sequences of the heavy chain and the light chain encoded by the SEQ ID NOS: 1 and 3, respectively.

The invention claimed is:

1. An anti-human PAI-1 antibody or an antigen-binding fragment thereof, comprising:
   a heavy chain variable region comprising CDR1 consisting of the amino acid sequence of amino acid numbers 31 to 35 of SEQ ID NO: 2, CDR2 consisting of the amino acid sequence of amino acid numbers 50 to 66 of SEQ ID NO: 2, and CDR3 consisting of the amino acid sequence of amino acid numbers 99 to 107 of SEQ ID NO: 2; and
   a light chain variable region comprising CDR1 consisting of the amino acid sequence of amino acid numbers 24 to 34 of SEQ ID NO: 4, CDR2 consisting of the amino acid sequence of amino acid numbers 50 to 56 of SEQ ID NO: 4, and CDR3 consisting of the amino acid sequence of amino acid numbers 89 to 97 of SEQ ID NO: 4.

2. The anti-human PAI-1 antibody or an antigen-binding fragment thereof according to claim 1, comprising a heavy chain variable region consisting of the amino acid sequence of amino acid numbers 1 to 118 of SEQ ID NO: 2, and a light chain variable region consisting of the amino acid sequence of amino acid numbers 1 to 108 of SEQ ID NO: 4.

3. The anti-human PAI-1 antibody or the antigen-binding fragment thereof according to claim 1, wherein the antibody or the antigen-binding fragment thereof comprises a heavy chain variable region consisting of the amino acid sequence of amino acid numbers 1 to 118 of SEQ ID NO: 2, in which glutamic acid at amino acid number 1 of SEQ ID NO: 2 is modified to pyroglutamic acid, and a light chain variable region consisting of the amino acid sequence of amino acid numbers 1 to 108 of SEQ ID NO: 4.

4. The anti-human PAI-1 antibody or an antigen-binding fragment thereof according to claim 2, which is selected from any one of the following (1) and (2):
   (1) an anti-human PAI-1 antibody comprising a heavy chain consisting of the amino acid sequence set forth in SEQ ID NO: 2 and a light chain consisting of the amino acid sequence set forth in SEQ ID NO: 4; and
   (2) an anti-human PAI-1 antibody comprising a heavy chain consisting of the amino acid sequence of SEQ ID NO: 2, in which glutamic acid of the amino acid number 1 of SEQ ID NO: 2 is modified to pyroglutamic acid and/or lysine of the amino acid number 448 of SEQ ID NO: 2 is deleted and a light chain consisting of the amino acid sequence set forth in SEQ ID NO: 4.

5. The anti-human PAI-1 antibody according to claim 4, comprising a heavy chain consisting of the amino acid sequence set forth in SEQ ID NO: 2, and a light chain consisting of the amino acid sequence set forth in SEQ ID NO: 4.

6. The anti-human PAI-1 antibody according to claim 4, comprising a heavy chain consisting of the amino acid sequence of amino acid numbers 1 to 447 of SEQ ID NO: 2, and a light chain consisting of the amino acid sequence set forth in SEQ ID NO: 4.

7. A pharmaceutical composition comprising
   (1) (a) anti-human PAI-1 antibody or antigen-binding fragment thereof according to claim 2, and/or
       (b) an anti-human PAI-1 antibody or an antigen-binding fragment thereof comprising a heavy chain variable region consisting of the amino acid sequence of amino acid numbers 1 to 118 of SEQ ID NO: 2, in which glutaminic acid of the amino acid number 1 of SEQ ID NO: 2 is modified to pyroglutamic acid, and a light chain variable region consisting of the amino acid sequence of amino acid numbers 1 to 108 of SEQ ID NO: 4, and (2) a pharmaceutically acceptable excipient.

8. A pharmaceutical composition comprising:
   (i)(a) the anti-human PAI-1 antibody according to claim 5 and/or
   (b) an anti-human PAI-1 antibody comprising a heavy chain consisting of the amino acid sequence of amino acid numbers 1 to 447 of SEQ ID NO: 2, and a light chain consisting of the amino acid sequence set forth in SEQ ID NO: 4, and (ii) a pharmaceutically acceptable excipient.

9. A polynucleotide comprising a base sequence encoding the heavy chain variable region of the anti-human PAI-1 antibody or the antigen-binding fragment thereof according to claim 2.

10. A polynucleotide comprising a base sequence encoding the light chain variable region of the anti-human PAI-1 antibody or the antigen-binding fragment thereof according to claim 2.

11. An expression vector comprising a polynucleotide comprising a base sequence encoding the heavy chain variable region of the anti-human PAI-1 antibody or the antigen-binding fragment thereof according to claim 2 and/or a polynucleotide comprising a base sequence encoding the light chain variable region of the anti-human PAI-1 antibody or the antigen-binding fragment thereof according to claim 2.

12. A host cell transformed with an expression vector, which is selected from the group consisting of the following (a) and (b):
  (a) a host cell transformed with an expression vector comprising a polynucleotide comprising a base sequence encoding the heavy chain variable region of the anti-human PAI-1 antibody or the antigen-binding fragment thereof according to claim 2 and a polynucleotide comprising a base sequence encoding the light chain variable region of the antibody or the antigen-binding fragment thereof; and
  (b) a host cell transformed with an expression vector comprising a polynucleotide comprising a base sequence encoding the heavy chain variable region of the anti-human PAI-1 antibody or the antigen-binding fragment thereof according to claim 2 and an expression vector comprising a polynucleotide comprising a base sequence encoding the light chain variable region of the antibody or the antigen-binding fragment thereof.

13. A host cell transformed with an expression vector, which is selected from the group consisting of the following (a) and (b):
  (a) a host cell transformed with an expression vector comprising a polynucleotide comprising a base sequence encoding the heavy chain of the anti-human PAI-1 antibody according to claim 5 and a polynucleotide comprising a base sequence encoding the light chain of the antibody; and
  (b) a host cell transformed with an expression vector comprising a polynucleotide comprising a base sequence encoding the heavy chain of the anti-human PAI-1 antibody according to claim 5 and an expression vector comprising a polynucleotide comprising a base sequence encoding the light chain of the antibody.

14. A method for producing an anti-human PAI-1 antibody or an antigen-binding fragment thereof, comprising culturing host cell(s) according to claim 12.

15. A method for producing an anti-human PAI-1 antibody, comprising culturing host cell(s) according to claim 13.

16. An anti-human PAI-1 antibody or an antigen-binding fragment thereof produced by the method according to claim 14.

17. An anti-human PAI-1 antibody produced by the method according to claim 15.

18. A pharmaceutical composition comprising the anti-human PAI-1 antibody or the antigen-binding fragment thereof according to claim 1, and a pharmaceutically acceptable excipient.

* * * * *

SEQUENCE LISTING

```
<160> NUMBER OF SEQ ID NOS: 5

<210> SEQ ID NO 1
<211> LENGTH: 1347
<212> TYPE: DNA
<213> ORGANISM: Artificial Sequence
<220> FEATURE:
<223> OTHER INFORMATION: H-chain gene of anti-human PAI-1 antibody
```

<220> FEATURE:
<221> NAME/KEY: CDS
<222> LOCATION: (1)..(1347)

<400> SEQUENCE: 1

```
gag gtg cag ctg gtg gag tct ggg gga ggt gtg gta cgg cct ggg ggg      48
Glu Val Gln Leu Val Glu Ser Gly Gly Gly Val Val Arg Pro Gly Gly
1               5                   10                  15 tcc ctg aga ctc tcc tgt gca gcc tct gga ttc acc ttt gat gat cat      96
Ser Leu Arg Leu Ser Cys Ala Ala Ser Gly Phe Thr Phe Asp Asp His
            20                  25                  30 ggc atg acc tgg gtc cgc caa gct cca ggg aag ggg ctg gag tgg gtc     144
Gly Met Thr Trp Val Arg Gln Ala Pro Gly Lys Gly Leu Glu Trp Val
        35                  40                  45 tct ggt att aat tgg aat ggt gct aga aca gtt tat gca gac tct gtg     192
Ser Gly Ile Asn Trp Asn Gly Ala Arg Thr Val Tyr Ala Asp Ser Val
    50                  55                  60 aag ggc cga ttc acc atc tcc aga gac aac gcc aag aac tcc ctc tat     240
Lys Gly Arg Phe Thr Ile Ser Arg Asp Asn Ala Lys Asn Ser Leu Tyr
65                  70                  75                  80 ctg cac ctg atc agt ctg aga gcc gag gac acg gcc ttg tat cac tgt     288
Leu His Leu Ile Ser Leu Arg Ala Glu Asp Thr Ala Leu Tyr His Cys
                85                  90                  95 gcg aga gat cgg gga ctg ggc ctc ttt gac tac tgg ggc cag gga acc     336
Ala Arg Asp Arg Gly Leu Gly Leu Phe Asp Tyr Trp Gly Gln Gly Thr
            100                 105                 110 ctg gtc acc gtc tcc tca gcc tcc acc aag ggc cca tcg gtc ttc ccc     384
Leu Val Thr Val Ser Ser Ala Ser Thr Lys Gly Pro Ser Val Phe Pro
        115                 120                 125 ctg gca ccc tcc tcc aag agc acc tct ggg ggc aca gcg gcc ctg ggc     432
Leu Ala Pro Ser Ser Lys Ser Thr Ser Gly Gly Thr Ala Ala Leu Gly
    130                 135                 140 tgc ctg gtc aag gac tac ttc ccc gaa ccg gtg acg gtg tcg tgg aac     480
Cys Leu Val Lys Asp Tyr Phe Pro Glu Pro Val Thr Val Ser Trp Asn
145                 150                 155                 160 tca ggc gcc ctg acc agc ggc gtg cac acc ttc ccg gct gtc cta cag     528
Ser Gly Ala Leu Thr Ser Gly Val His Thr Phe Pro Ala Val Leu Gln
                165                 170                 175 tcc tca gga ctc tac tcc ctt agt agc gtg gtg acc gtg ccc tcc agc     576
Ser Ser Gly Leu Tyr Ser Leu Ser Ser Val Val Thr Val Pro Ser Ser
            180                 185                 190 agc ttg ggc acc cag acc tac atc tgc aac gtg aat cac aag ccc agc     624
Ser Leu Gly Thr Gln Thr Tyr Ile Cys Asn Val Asn His Lys Pro Ser
        195                 200                 205 aac acc aag gtg gac aag aaa gtt gag ccc aaa tct tgt gac aaa act     672
Asn Thr Lys Val Asp Lys Lys Val Glu Pro Lys Ser Cys Asp Lys Thr
    210                 215                 220 cac aca tgc cca ccg tgc cca gca cct gaa ctc ctg ggg gga ccg tca     720
His Thr Cys Pro Pro Cys Pro Ala Pro Glu Leu Leu Gly Gly Pro Ser
225                 230                 235                 240 gtc ttc ctc ttc ccc cca aaa ccc aag gac acc ctc atg atc tcc cgg     768
Val Phe Leu Phe Pro Pro Lys Pro Lys Asp Thr Leu Met Ile Ser Arg
                245                 250                 255 acc cct gag gtc aca tgc gtg gtg gtg gac gtg agc cac gaa gac cct     816
Thr Pro Glu Val Thr Cys Val Val Val Asp Val Ser His Glu Asp Pro
            260                 265                 270 gag gtc aag ttc aac tgg tac gtg gac ggc gtg gag gtg cat aat gcc     864
Glu Val Lys Phe Asn Trp Tyr Val Asp Gly Val Glu Val His Asn Ala
        275                 280                 285
```

```
aag aca aag ccg cgg gag gag cag tac aac agc acg tac cgt gtg gtc      912
Lys Thr Lys Pro Arg Glu Glu Gln Tyr Asn Ser Thr Tyr Arg Val Val
    290             295                 300 agc gtc ctc acc gtc ctg cac cag gac tgg ctg aat ggc aag gag tac      960
Ser Val Leu Thr Val Leu His Gln Asp Trp Leu Asn Gly Lys Glu Tyr
305             310                 315                 320 aag tgc aag gtc tcc aac aaa gcc ctc cca gcc ccc atc gag aaa acc     1008
Lys Cys Lys Val Ser Asn Lys Ala Leu Pro Ala Pro Ile Glu Lys Thr
                325                 330                 335 atc tcc aaa gcc aaa ggg cag ccc cga gaa cca cag gtg tac acc ctg     1056
Ile Ser Lys Ala Lys Gly Gln Pro Arg Glu Pro Gln Val Tyr Thr Leu
            340                 345                 350 ccc cca tcc cgg gat gag ctg acc aag aac cag gtc agc ctg acc tgc     1104
Pro Pro Ser Arg Asp Glu Leu Thr Lys Asn Gln Val Ser Leu Thr Cys
                355                 360                 365 ctg gtc aaa ggc ttc tat ccc agc gac atc gcc gtg gag tgg gag agc     1152
Leu Val Lys Gly Phe Tyr Pro Ser Asp Ile Ala Val Glu Trp Glu Ser
370             375                 380 aat ggg cag ccg gag aac aac tac aag acc acg cct ccc gtg ctg gac     1200
Asn Gly Gln Pro Glu Asn Asn Tyr Lys Thr Thr Pro Pro Val Leu Asp
385             390                 395                 400 tcc gac ggc tcc ttc ttc ctc tac agc aag ctc acc gtg gac aag agc     1248
Ser Asp Gly Ser Phe Phe Leu Tyr Ser Lys Leu Thr Val Asp Lys Ser
                405                 410                 415 agg tgg cag cag ggg aac gtc ttc tca tgc tcc gtg atg cat gag gct     1296
Arg Trp Gln Gln Gly Asn Val Phe Ser Cys Ser Val Met His Glu Ala
            420                 425                 430 ctg cac aac cac tac acg cag aag agc ctc tcc ctg tct ccg ggt aaa     1344
Leu His Asn His Tyr Thr Gln Lys Ser Leu Ser Leu Ser Pro Gly Lys
                435                 440                 445 tga                                                                  1347

<210> SEQ ID NO 2
<211> LENGTH: 448
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp His
            20                  25                  30

Gly Met Thr Trp Val Arg Gln Ala Pro Gly Lys Gly Leu Glu Trp Val
        35                  40                  45

Ser Gly Ile Asn Trp Asn Gly Ala Arg Thr Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu His Leu Ile Ser Leu Arg Ala Glu Asp Thr Ala Leu Tyr His Cys
                85                  90                  95

Ala Arg Asp Arg Gly Leu Gly Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 3
<211> LENGTH: 645
<212> TYPE: DNA
<213> ORGANISM: Artificial Sequence
<220> FEATURE:
<223> OTHER INFORMATION: L-chain of anti-human PAI-1 antibody
<220> FEATURE:
<221> NAME/KEY: CDS
<222> LOCATION: (1)..(645)

<400> SEQUENCE: 3 gac atc cag atg acc cag tct cct tcc acc ctg tct gca tct gta gga      48
Asp Ile Gln Met Thr Gln Ser Pro Ser Thr Leu Ser Ala Ser Val Gly
1               5                   10                  15 gac aga gtc acc atc act tgc cgg gcc agt cag agt att agt agc tgg      96
Asp Arg Val Thr Ile Thr Cys Arg Ala Ser Gln Ser Ile Ser Ser Trp
            20                  25                  30
```

| | | | | | | | | | | | | | | | | |
|---|---|---|---|---|---|---|---|---|---|---|---|---|---|---|---|---|
|ttg|gcc|tgg|tat|cag|cag|aaa|cca|ggg|aaa|gtc|cct|aag|atc|ctg|atc|144|
|Leu|Ala|Trp|Tyr|Gln|Gln|Lys|Pro|Gly|Lys|Val|Pro|Lys|Ile|Leu|Ile| |
| | |35| | | |40| | | |45| | | | | | |

| | | | | | | | | | | | | | | | | |
|---|---|---|---|---|---|---|---|---|---|---|---|---|---|---|---|---|
|tat|aag|gcg|tct|aga|ttg|gaa|agt|ggg|gtc|cca|tca|agg|atc|agc|ggc|192|
|Tyr|Lys|Ala|Ser|Arg|Leu|Glu|Ser|Gly|Val|Pro|Ser|Arg|Ile|Ser|Gly| |
|50| | | | |55| | | | |60| | | | | | |

| | | | | | | | | | | | | | | | | |
|---|---|---|---|---|---|---|---|---|---|---|---|---|---|---|---|---|
|agt|gga|tct|ggg|aca|gaa|ttc|act|ctc|acc|atc|agc|agc|ctg|cag|cct|240|
|Ser|Gly|Ser|Gly|Thr|Glu|Phe|Thr|Leu|Thr|Ile|Ser|Ser|Leu|Gln|Pro| |
|65| | | | |70| | | | |75| | | | |80| |

| | | | | | | | | | | | | | | | | |
|---|---|---|---|---|---|---|---|---|---|---|---|---|---|---|---|---|
|gat|gat|ttt|gca|act|tat|tac|tgc|caa|cag|tat|aat|ggt|tat|tcg|tac|288|
|Asp|Asp|Phe|Ala|Thr|Tyr|Tyr|Cys|Gln|Gln|Tyr|Asn|Gly|Tyr|Ser|Tyr| |
| | | | |85| | | | |90| | | | |95| | |

| | | | | | | | | | | | | | | | | |
|---|---|---|---|---|---|---|---|---|---|---|---|---|---|---|---|---|
|act|ttt|ggc|cag|ggg|acc|aag|ctg|gag|atc|aaa|cgt|acg|gtg|gct|gca|336|
|Thr|Phe|Gly|Gln|Gly|Thr|Lys|Leu|Glu|Ile|Lys|Arg|Thr|Val|Ala|Ala| |
| | | | |100| | | | |105| | | | |110| | |

| | | | | | | | | | | | | | | | | |
|---|---|---|---|---|---|---|---|---|---|---|---|---|---|---|---|---|
|cca|tct|gtc|ttc|atc|ttc|ccg|cca|tct|gat|gag|cag|ttg|aaa|tct|gga|384|
|Pro|Ser|Val|Phe|Ile|Phe|Pro|Pro|Ser|Asp|Glu|Gln|Leu|Lys|Ser|Gly| |
| | | | |115| | | | |120| | | | |125| | |

| | | | | | | | | | | | | | | | | |
|---|---|---|---|---|---|---|---|---|---|---|---|---|---|---|---|---|
|act|gcc|tct|gtt|gtg|tgc|ctg|ctg|aat|aac|ttc|tat|ccc|aga|gag|gcc|432|
|Thr|Ala|Ser|Val|Val|Cys|Leu|Leu|Asn|Asn|Phe|Tyr|Pro|Arg|Glu|Ala| |
|130| | | | |135| | | | |140| | | | | | |

| | | | | | | | | | | | | | | | | |
|---|---|---|---|---|---|---|---|---|---|---|---|---|---|---|---|---|
|aaa|gta|cag|tgg|aag|gtg|gat|aac|gcc|ctc|caa|tcg|ggt|aac|tcc|cag|480|
|Lys|Val|Gln|Trp|Lys|Val|Asp|Asn|Ala|Leu|Gln|Ser|Gly|Asn|Ser|Gln| |
|145| | | | |150| | | | |155| | | | |160| |

| | | | | | | | | | | | | | | | | |
|---|---|---|---|---|---|---|---|---|---|---|---|---|---|---|---|---|
|gag|agt|gtc|aca|gag|cag|gac|agc|aag|gac|agc|acc|tac|agc|ctg|agc|528|
|Glu|Ser|Val|Thr|Glu|Gln|Asp|Ser|Lys|Asp|Ser|Thr|Tyr|Ser|Leu|Ser| |
| | | | |165| | | | |170| | | | |175| | |

| | | | | | | | | | | | | | | | | |
|---|---|---|---|---|---|---|---|---|---|---|---|---|---|---|---|---|
|agc|acc|ctg|acg|ctg|agc|aaa|gca|gac|tac|gag|aaa|cac|aaa|gtc|tac|576|
|Ser|Thr|Leu|Thr|Leu|Ser|Lys|Ala|Asp|Tyr|Glu|Lys|His|Lys|Val|Tyr| |
| | | |180| | | | |185| | | | |190| | | |

| | | | | | | | | | | | | | | | | |
|---|---|---|---|---|---|---|---|---|---|---|---|---|---|---|---|---|
|gcc|tgc|gaa|gtc|acc|cat|cag|ggc|ctg|agc|tcg|ccc|gtc|aca|aag|agc|624|
|Ala|Cys|Glu|Val|Thr|His|Gln|Gly|Leu|Ser|Ser|Pro|Val|Thr|Lys|Ser| |
| | | |195| | | | |200| | | | |205| | | |

| | | | | |
|---|---|---|---|---|
|ttc|aac|agg|gga|gag|tgt|tag|645|
|Phe|Asn|Arg|Gly|Glu|Cys| | |
| |210| | | | | | |

<210> SEQ ID NO 4
<211> LENGTH: 214
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Val Pro Lys Ile Leu Ile
        35                  40                  45

Tyr Lys Ala Ser Arg Leu Glu Ser Gly Val Pro Ser Arg Ile Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Gly Tyr Ser Tyr
                85                  90                  95

Thr Phe Gly Gln Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 5
<211> LENGTH: 16
<212> TYPE: PRT
<213> ORGANISM: Homo sapiens

<400> SEQUENCE: 5

Ser Thr Ala Val Ile Val Ser Ala Arg Met Ala Pro Glu Glu Ile Ile
1               5                   10                  15
```